(12) United States Patent
Kawai

(10) Patent No.: US 8,214,083 B2
(45) Date of Patent: Jul. 3, 2012

(54) MANIPULATOR

(75) Inventor: Toshimasa Kawai, Yokohama (JP)

(73) Assignee: Olympus Medical Systems Corp., Tokyo (JP)

( * ) Notice: Subject to any disclaimer, the term of this patent is extended or adjusted under 35 U.S.C. 154(b) by 128 days.

(21) Appl. No.: 12/828,709

(22) Filed: Jul. 1, 2010

(65) Prior Publication Data
US 2011/0015786 A1 Jan. 20, 2011

Related U.S. Application Data

(63) Continuation of application No. PCT/JP2010/050342, filed on Jan. 14, 2010.

(30) Foreign Application Priority Data

Feb. 3, 2009 (JP) ................................. 2009-023032

(51) Int. Cl.
G05B 19/04 (2006.01)
B25J 18/06 (2006.01)
(52) U.S. Cl. ...................... 700/256; 74/490.04; 600/118
(58) Field of Classification Search .................. 700/256, 700/245, 250, 257, 259, 260, 264; 901/14, 901/15, 17, 23, 25, 41, 47; 74/490.03, 490.04; 600/102, 109, 118, 139, 146
See application file for complete search history.

(56) References Cited

U.S. PATENT DOCUMENTS

| 5,986,424 | A | | 11/1999 | Nakatsuka et al. | |
| 6,110,127 | A | * | 8/2000 | Suzuki | 600/565 |
| 7,104,953 | B2 | * | 9/2006 | Hirata et al. | 600/152 |
| 7,109,678 | B2 | * | 9/2006 | Kraus et al. | 318/560 |
| 2008/0262306 | A1 | | 10/2008 | Kawai | |
| 2010/0105980 | A1 | * | 4/2010 | Shimizu et al. | 600/101 |
| 2010/0210908 | A1 | * | 8/2010 | Ashida et al. | 600/145 |
| 2011/0009698 | A1 | * | 1/2011 | Ashida et al. | 600/118 |
| 2011/0065993 | A1 | * | 3/2011 | Belson et al. | 600/141 |
| 2011/0196199 | A1 | * | 8/2011 | Donhowe et al. | 600/102 |
| 2011/0282351 | A1 | * | 11/2011 | Cooper et al. | 606/108 |
| 2012/0022553 | A1 | * | 1/2012 | Cooper et al. | 606/130 |

FOREIGN PATENT DOCUMENTS

EP 1 972 257 A1 9/2008

(Continued)

OTHER PUBLICATIONS

International Search Report dated Feb. 16, 2010.

Primary Examiner — Khoi Tran
Assistant Examiner — Jason Holloway
(74) Attorney, Agent, or Firm — Scully, Scott, Murphy & Presser, P.C.

(57) ABSTRACT

A manipulator comprises a tube body including a bending portion, a bending wire for a bending drive of the bending portion, a motor including a rotary shaft which rotates in accordance with a drive command signal, a reduction gear unit connected to the rotary shaft and configured by a plurality of gears meshing with each other, a detection unit which detects an operation state of the motor, a storage unit which stores load variation values periodically caused by the meshing of the plurality of gears constituting the reduction gear unit as correction information, a load calculation section which calculates a load exerted on the tube body as a bending load estimated value, and a notifying unit which notifies a calculation result of the load calculation section.

8 Claims, 25 Drawing Sheets

FOREIGN PATENT DOCUMENTS

| | | |
|---|---|---|
| JP | 08-286759 | 11/1996 |
| JP | 10-243676 | 9/1998 |
| JP | 2002-315720 | 10/2002 |
| JP | 2003-256004 | 9/2003 |
| JP | 2005-100145 | 4/2005 |
| JP | 2006-055927 | 3/2006 |
| JP | 2007-185355 | 7/2007 |
| WO | WO 2007/080953 A1 | 7/2007 |

* cited by examiner

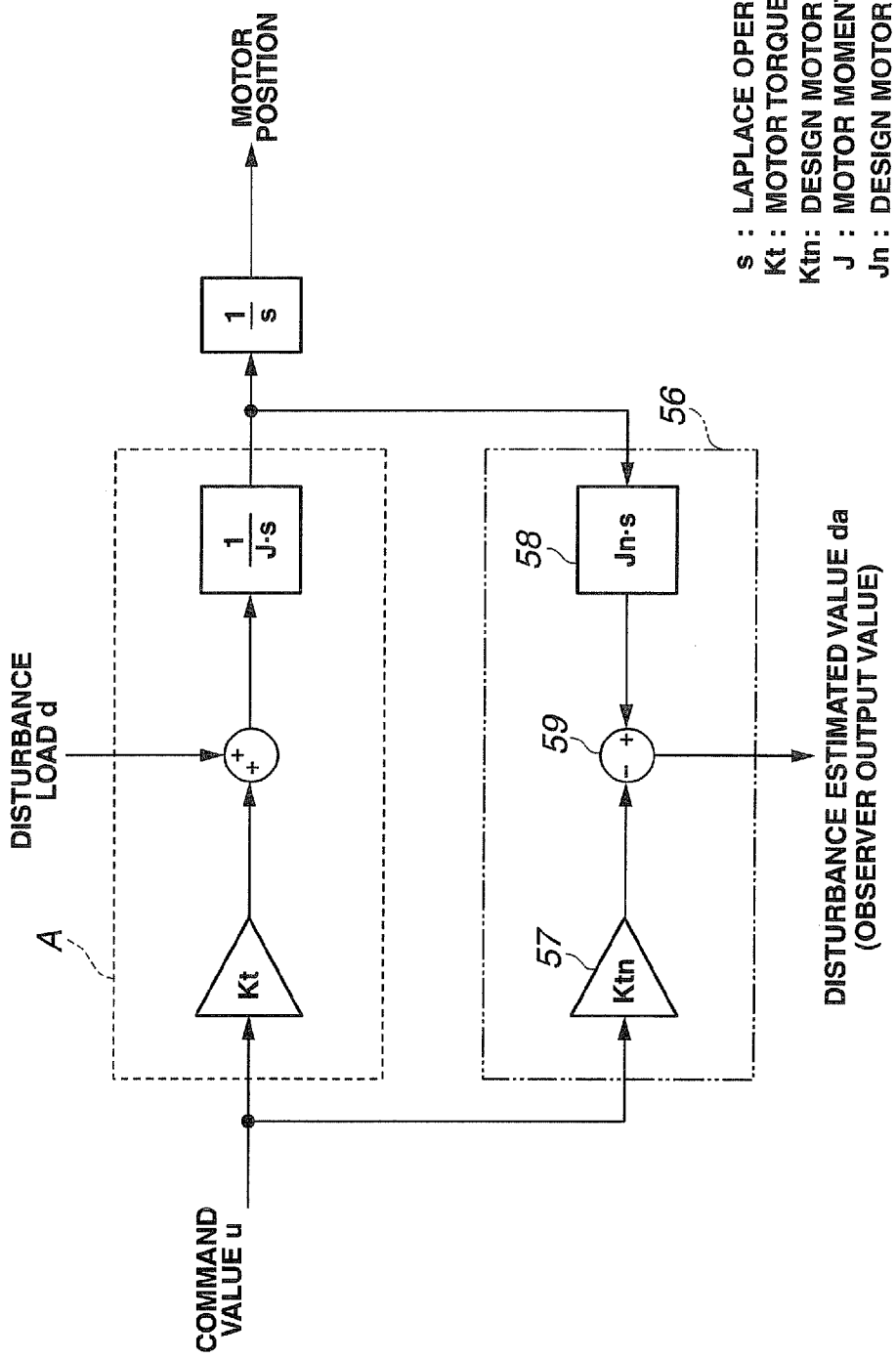

66a  66b  66a  66b  66a  66b

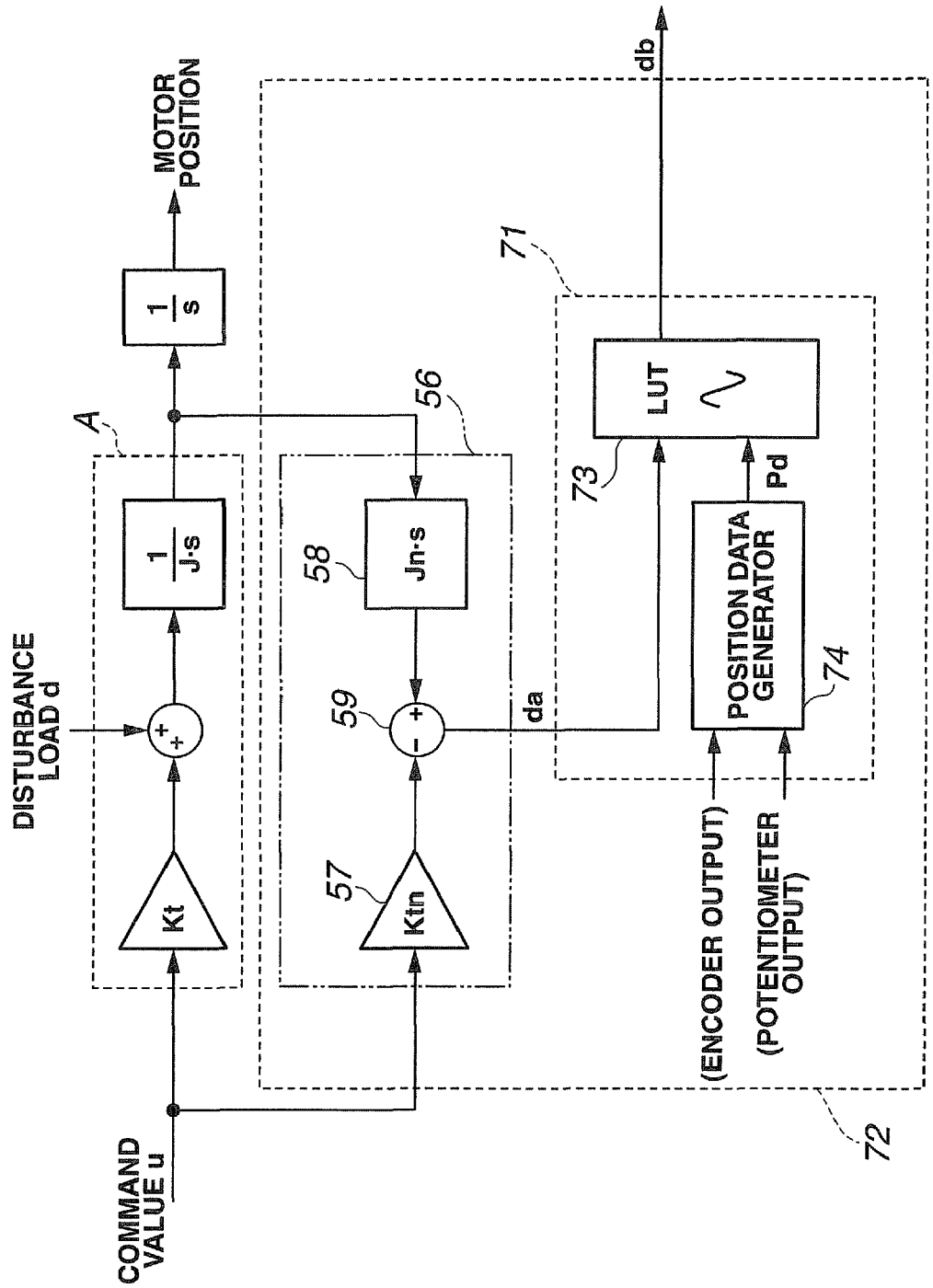

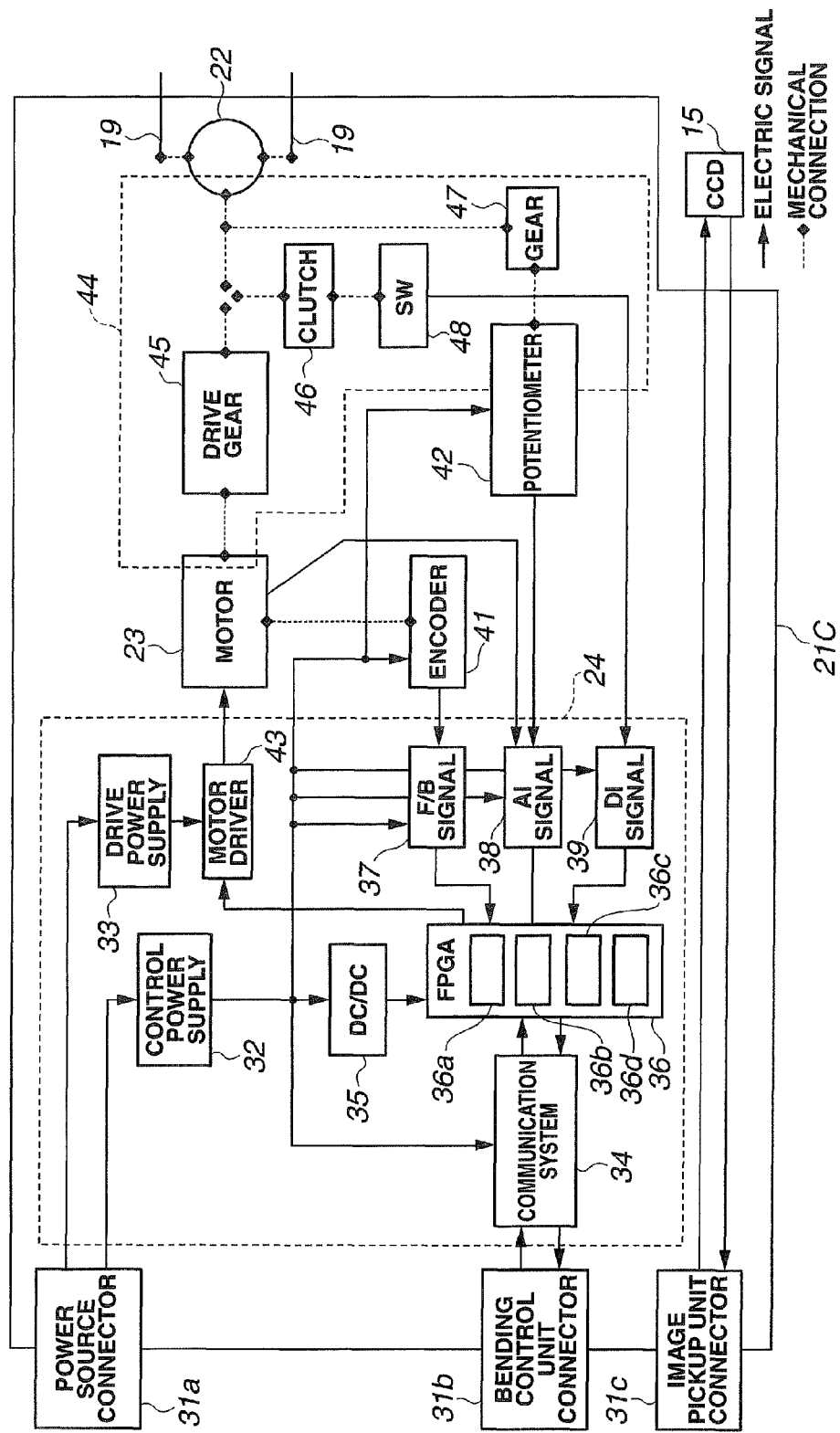

MANIPULATOR

CROSS REFERENCE TO RELATED APPLICATION

This application is a continuation application of PCT/JP2010/050342 filed on Jan. 14, 2010 and claims benefit of Japanese Application No. 2009-023032 filed in Japan on Feb. 3, 2009, the entire contents of which are incorporated herein by this reference.

BACKGROUND OF THE INVENTION

1. Field of the Invention

The present invention relates to a manipulator for performing a bending operation of a bending portion, etc.

2. Description of the Related Art

Generally, various kinds of electric instruments using motors as driving means have been widely used. With respect to an endoscope, for instance, as a medical instrument, in addition to an endoscope of a manual operation system in which a bending section provided in an insertion portion to be inserted into a body cavity is manually driven, an endoscope of an electric driving system in which a motor is used as driving means for improving operability has been brought into practical use.

In a case of driving a load by a motor, a sensor for detecting a state of the load is usually used as well as detecting means for detecting an operation state of the motor. For example, in a case of an endoscope, if a sensor for detecting a tensile force acting on the bending portion to drive the bending portion is provided, the insertion portion is made thick or a necessity arises, for example, to make a structure of the sensor have durability with respect to cleaning and disinfecting, which increases cost.

Therefore, technique of a disturbance observer that calculates a disturbance exerted on an output shaft of a motor (a component excluding a driving force generated by the motor itself) from a rotational velocity of the output shaft, etc. by operation processing using software is described in Japanese Patent Laid-Open Publication No. 2007-185355.

As described, by adopting a method of the disturbance observer, a load value of a motor can be calculated as a disturbance estimated value without using a sensor, to eliminate cost increase, etc.

Note that in driving a load side such as bending portion by the motor, a reduction gear unit is used for sufficiently driving the load.

SUMMARY OF THE INVENTION

A manipulator according to an aspect of the present invention comprises:

an elongated tube body including a bendable bending portion;

a bending wire provided at the tube body for bending operation of the bending portion;

a motor including a rotary shaft which rotates in accordance with a drive command signal;

a reduction gear unit connected to the rotary shaft and configured by a plurality of gears meshing with each other for changing velocity with respect to a rotational velocity of the rotary shaft;

a connection portion which connects a proximal end of the bending wire and the reduction gear unit for operating the bending portion;

a detection unit which detects an operation state of the motor rotationally driven in accordance with the drive command signal;

a storage unit which stores load variation values periodically caused by the meshing of the plurality of gears constituting the reduction gear unit, as correction information;

a load calculation section which calculates a load exerted on the tube body as a bending load estimated value based on drive prediction information of the motor supposed by a drive signal supplied to the motor, the operation state information of the motor detected by the detection unit and the correction information stored in the storage unit; and a notification unit which notifies a calculation result of the load calculation section as the bending load estimated value.

A manipulator according to another aspect of the present invention comprises:

an elongated tube body including a bendable bending portion;

a bending wire provided at the tube body for bending operation of the bending portion;

a motor including a rotary shaft which rotates in accordance with a drive command signal;

a reduction gear unit connected to the rotary shaft and configured by a plurality of gears meshing with each other for changing velocity with respect to a rotational velocity of the rotary shaft;

a connection portion which connects a proximal end of the bending wire and the reduction gear unit for operating the bending portion;

a detection unit which detects operation states of the motor rotationally driven in accordance with the drive command signal and the reduction gear unit;

a load calculation section which calculates a load exerted on the tube body as a bending load estimated value based on drive prediction information of the motor supposed by a drive signal supplied to the motor, the operation state information of the motor detected by the detection unit; and a notification unit which notifies a calculation result of the load calculation section as the bending load estimated value.

BRIEF DESCRIPTION OF THE DRAWINGS

FIG. 4 is a block diagram showing a principle of load calculation by a disturbance observer used in the embodiment;

FIG. 9 is a block diagram showing a configuration of calculating a disturbance estimated value using a technique of disturbance observer in the embodiment 1;

FIG. 14 is a block diagram showing a configuration of a motor unit of embodiment 3 of the present invention;

DETAILED DESCRIPTION OF THE PREFERRED EMBODIMENT(S)

Figure 1:
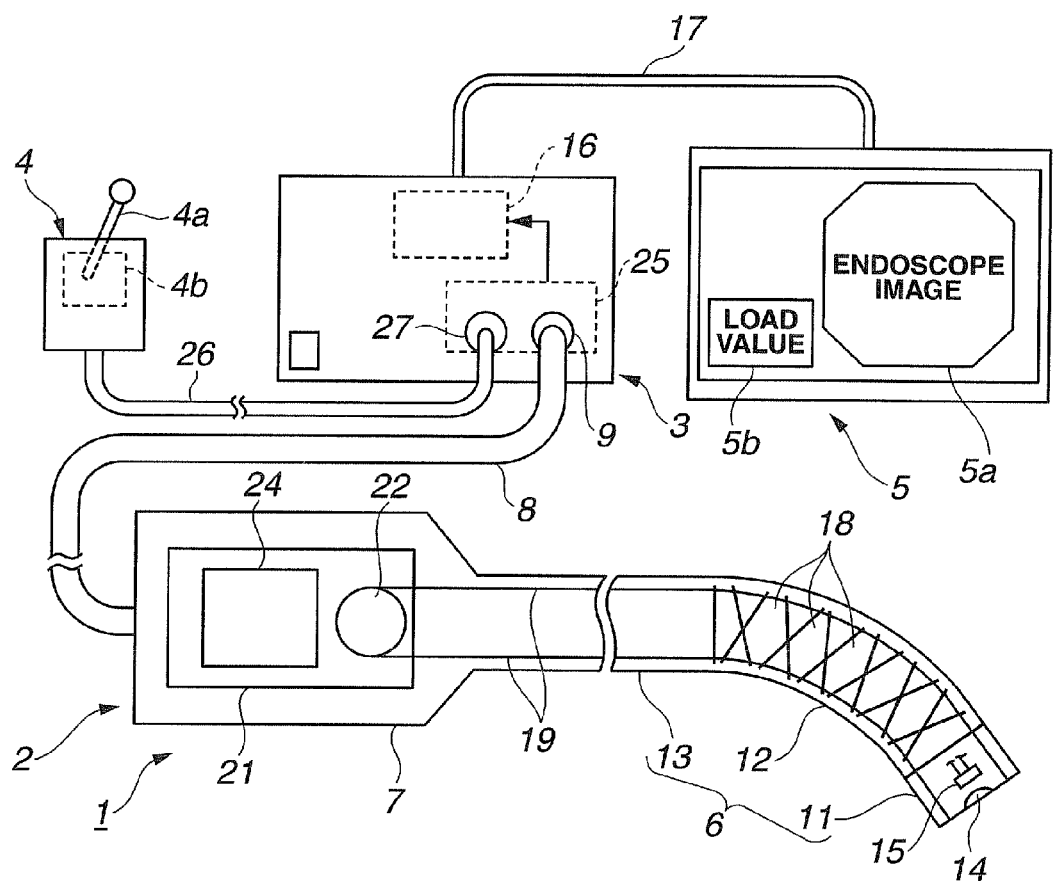
FIG. 1 is a view showing an entire configuration of an endoscope system including embodiment 1 of the present invention.

Hereinafter, embodiments of the present invention will be described referring to the drawings.

As shown in FIG. 1, an endoscope system 1 including embodiment 1 of the present invention has an endoscope 2 to be inserted into a subject, a controller 3 to which the endoscope 2 is connected, an operation commanding unit 4 connected to the controller 3 for performing a bending command operation, and an endoscope monitor 5 for performing a display of an endoscope image, etc.

The endoscope 2 comprises an insertion portion 6 to be inserted into a subject and having a shape of an elongated cylindrical tube, an operation portion 7 provided at a rear end of the insertion portion 6 and a universal cable 8 extending from the operation portion 7, and a connector 9 at an end of the universal cable 8 is connected to a plug of the controller 3 detachably.

The insertion portion 6 has a distal end portion 11 provided at a distal end thereof, a bendable bending portion 12 provided at a rear end of the distal end portion 11, and an elongated flexible portion 13 which has flexibility and extends from a rear end of the bending portion 12 to a front end of the operation portion 7.

The distal end portion 11 is provided with an illumination window, which is not shown, for emitting illumination light, and an observation window in the vicinity of the illumination window, and an objective lens 14 is attached to the observation window. Thus, the objective lens 14 forms an optical image of a target part of observation in the subject illuminated by the illumination light.

A charge-coupled device (abbreviated as CCD) 15, for example, is located at an image forming position of the objective lens 14 to form an image pick-up portion for picking-up an image of a target part of observation in the subject. This CCD 15 is connected to a video signal generation unit 16 provided in the controller 3 which is external of the endoscope 2.

The video signal generation unit 16 drives the CCD 15 and performs signal processing of an image pick-up signal which is obtained by photoelectric transformation by the CCD 15, to generate a video signal and outputs the video signal to an endoscope monitor 5 through a monitor cable 17. The endoscope monitor 5 displays an endoscope image corresponding to an optical image formed on an image pick-up surface of the CCD 15 on an endoscope image display unit 5a.

The above bending portion 12 is configured such that a plurality of bending pieces 18, 18, . . . , 18 having approximately annular shapes as movable bodies are connected successively to be rotatable and in the longitudinal direction to form a tube body having a cylindrical tube shape. Pivotal portions for successive connection to be rotatable are provided at positions corresponding to vertical directions and horizontal directions of the bending portion 12.

Further, bending wires 19, 19 for transmitting a driving force for bending the bending pieces 18, 18, . . . , 18 are inserted in and through the insertion portion 6 along inner walls corresponding to vertical bending directions, e.g., of the bending portion 12.

In addition, in FIG. 1, etc. only the bending wires 19, 19 as a pair for bending, e.g. in vertical directions are shown for simplification, however, in a case of bending the insertion portion in the horizontal directions, bending wires 19, 19 as a pair are inserted in and through the insertion portion in the same manner along the horizontal directions. Distal ends of the bending wires 19, 19 as the pair are fixed to the bending piece 18 at the front end or the distal end portion 11.

Rear ends of the bending wires 19, 19 as the pair are located in the operation portion 7 and are engaged with a sprocket 22 in a motor unit 21. In addition, this manipulator is configured mainly by the motor unit 21, the bending wires 19, 19, and the bending portion 12. In the present embodiment, since a display monitor 5 serves as a component for displaying a load value, as shown in FIG. 1, the endoscope system 1 of FIG. 1 can be regarded as a configuration example of the manipulator.

By rotationally driving the above-mentioned sprocket 22 by a motor 23 (see FIG. 2) in the motor unit 21, one of the pair of bending wires 19, 19 engaged with the sprocket 22 is pulled and the other of the pair of bending wires 19, 19 is released. Then, the bending pieces 18, 18, ..., 18 as the movable bodies of the bending portion 12 are bent in the direction of the wire 19 which is pulled.

In addition, although the sprocket 22, the motor 23, etc. for the bending drive in the vertical directions, for example, are shown in a case of bending in the horizontal directions, those of the same configuration are provided.

As described later, a rotational driving force by the motor 23 is transmitted to the sprocket 22 through a planetary gear reduction mechanism 44 which forms a reduction gear unit. Therefore, an influence of a meshing backlash between gears in the planetary gear reduction mechanism 44 and so forth is caused, but the motor unit 21 has configuration of reducing the influence and performing a bending drive control of the bending portion 12.

This motor unit 21 comprises a large-scale integration circuit portion (abbreviated as LSI portion) 24 with a function of a load calculation section 72, as described later, for performing calculation processing for load calculation of the motor 23, and this LSI portion 24 is connected to a control unit 25 in the controller 3 through a cable inserted in the universal cable 8.

Further, the operation commanding unit 4 is connected to the controller 3 through an operation commanding unit cable (abbreviated as operation cable) 26 such that a connector 27, which is an end of the operation cable 26, is detachably connected to the controller 3.

The operation commanding unit 4 is provided with a joystick 4a, for example, for performing an operation command of a bending direction and a bending amount by an inclination direction and an inclination angle (inclination amount). A proximal end side of this joystick 4a is supported to be inclinable and a sensor 4b such as a potentiometer for detecting inclination direction and inclination angle of the joystick 4a is provided.

Then, the sensor 4b transmits (outputs) a detection value to the control unit 25 as a command signal by the operation commanding unit 4 through the operation cable 26.

Upon receipt of a command signal from the operation commanding unit 4, the control unit 25 transmits (outputs) the command signal to the LSI portion 24 in the motor unit 21 through a cable in the universal cable 8.

Then, the LSI portion 24 provides a command value as a drive command signal for rotationally driving the motor 23 according to a command signal, takes in a current value and position information etc. by detection units (an encoder 41, etc. as described later) when rotationally driving the motor 23, and performs a feedback control so as to coincide with command values.

In this case, when the bending portion 12 is bending-driven by the motor 23 through the bending wires 19, 19, a tension amount as a load in pulling the bending wires 19, 19 can be detected by a sensor such as a distortion sensor. However, since provision of such a sensor makes the insertion portion thick, in the present embodiment, without providing a sensor, a load or a load value is calculated using a method of a disturbance observer and using software disturbance estimation means.

Further, the calculated load value is outputted to the control unit 25 and the control unit 25 outputs the inputted load value to the video signal generation unit 16. The video signal generation unit 16 superposes information of the inputted load value with the video signal, for example, and outputs the superposed video signal to the endoscope monitor 5, so that the calculated value is displayed on a load value display portion 5b in the endoscope monitor 5. Thus, a notifying portion for notifying the load value visually is formed.

The notifying portion for notifying the calculated load value is not restricted to a case of notification by display, and may be performed by presentation of a force sense corresponding to the calculated load value to the operation commanding unit 4 from the control unit 25. The notification may be performed, for example, by providing a rotary shaft of the joystick 4a with a motor to be driven by a reaction amount corresponding to the calculated load value, or by disposing a vibration motor, etc. at the operation commanding unit 4 and vibrating the vibration motor in accordance with the load vale, etc.

Figure 2:
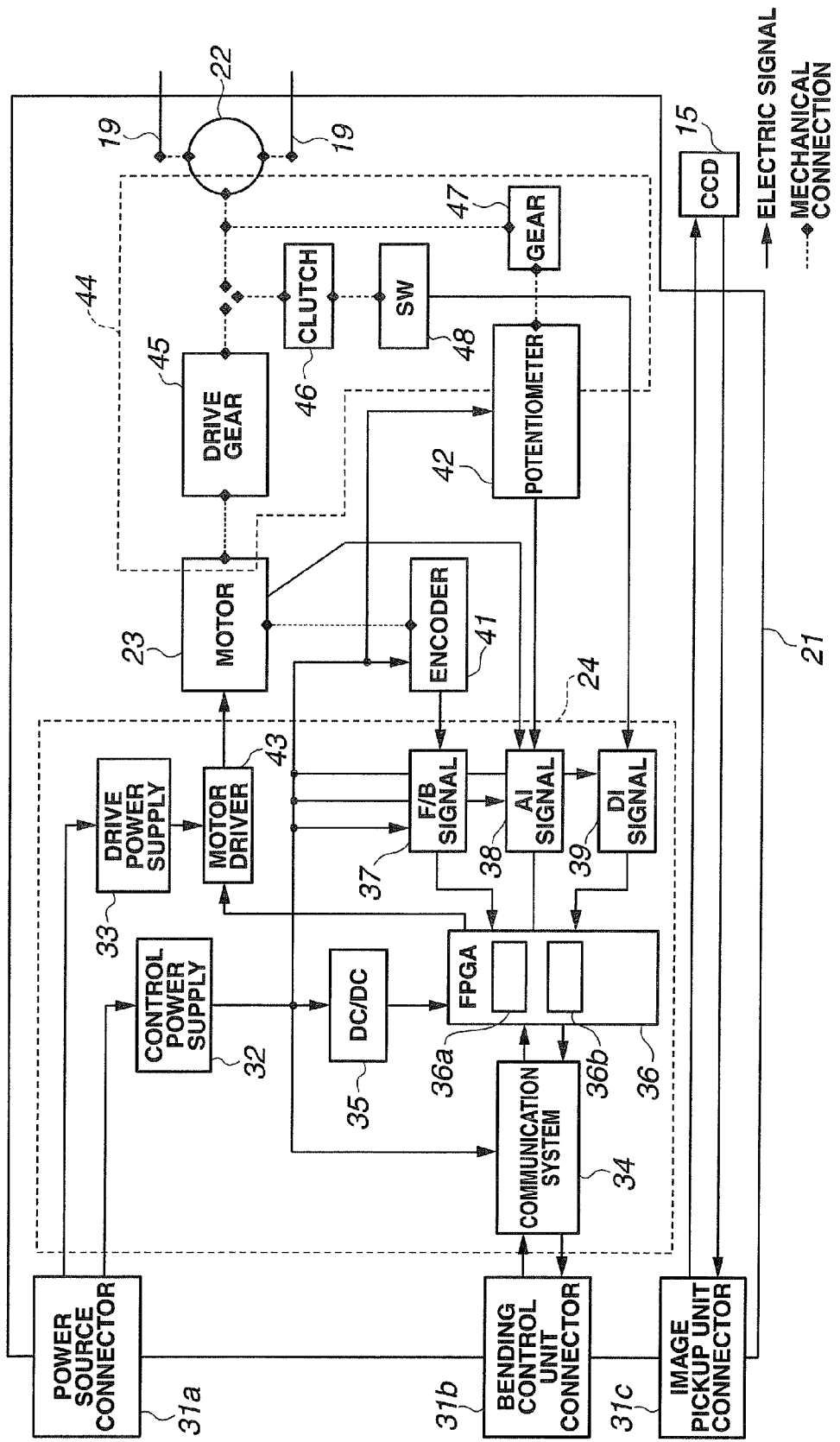
FIG. 2 is a block diagram showing a configuration of a motor unit provided in the endoscope of FIG. 1.

FIG. 2 shows a detailed configuration of the motor unit 21.

The motor unit 21 is provided with a power source connector 31a, a bending control unit connector 31b and an image pick-up portion connector 31c to which ends of cables, which are not shown and inserted in and through the universal cable 8, are connected.

The power source connector 31a connected with the cable for supplying electric power from the controller 3 respectively supplies driving powers to a control power supply circuit 32 and a drive power supply circuit 33 in the LSI portion 24.

The control power supply circuit 32 generates control power and supplies the generated power to a communication-system block 34 in the LSI portion 24 and an FPGA (Field Programmable Gate Array) block 36, etc. through a DC/DC converter 35.

Further, the control power is supplied to a feedback signal input section (abbreviated as FB signal in FIG. 2) 37, an analog input signal input section (abbreviated as AI signal in FIG. 2) 38, and a digital input signal input section (abbreviated as DI signal in FIG. 2) 39, and also to an encoder 41 and a potentiometer 42 external of the LSI portion 24.

The DC/DC converter 35 generates a high-voltage DC from the direct-current DC power supply and supplies the high-voltage DC to the FPGA block 36 as a programmable LSI which requires a high-voltage DC power.

The drive power supply circuit 33 generates a drive power and supplies the drive power to a motor driver 43 (which rotates a motor 23 by a command value as a drive command signal).

The communication-system block 34 connected to the bending control section connector 31b forms an interface for performing interactive communication between the control unit 25 in FIG. 1 and the FPGA block 36. For example, a command signal generated in the operation commanding unit 4 is transmitted from the control unit 25 to the FPGA block 36 through the communication-system block 34, and the FPGA block 36 supplies a command value to the motor 23 from the command signal through the motor driver 43.

Further, a load value calculated by the FPGA block 36 is transmitted to the control unit 25 through the communication-system block 34. Then, as described above, the load value is notified by display.

The image pick-up portion connector 31c is connected to the CCD 15 through a signal line. Note that the image pick-up portion connector 31c may be formed separately from the motor unit 21.

The motor 23 which is rotationally driven by the motor driver 43 is mechanically engaged with the sprocket 22 through the planetary gear reduction mechanism 44.

In the planetary gear reduction mechanism 44, a drive gear 45 is directly connected to a motor shaft (rotary shaft) of the motor 23 and the drive gear 45 meshes with a gear 47 connected to a rotary shaft of the sprocket 22 through a clutch 46. Then, out of mesh (interrupt) and in mesh (meshed connection state) states are brought by a switch 48 for performing ON/OFF of the clutch 46.

The ON/OFF signal of the switch 48 is inputted to the FPGA block 36 as a digital input signal through the digital input signal input section 39.

The potentiometer 42 connected with a rotary shaft of the gear 47 detects a rotational position of the gear 47 and position information thereof is inputted to the FPGA block 36 as an analog input signal through the analog input signal input section 38. Thus, the potentiometer 42 forms a position (information) detection unit of the gear 47 constituting the reduction gear unit.

The rotational position (rotary motion position) of the motor 23 is detected by the encoder 41 connected to the motor shaft (i.e. rotary shaft). The position information detected by the encoder 41 is inputted to the FPGA block 36 as a feedback signal through the feedback signal input section 37. The encoder 41 forms a detection unit of the rotational position of the drive gear 45 connected to the motor shaft.

A value of a current flowing through the motor 23 is inputted to the FPGA block 36 as an analog input signal through the analog input signal input section 38.

Means for detecting values of currents flowing through the encoder 41 and the motor 23 form a detection unit for detecting a rotational position, a rotational velocity, etc. of the motor 23 as an operational state of the motor 23.

The FPGA block 36 forms a manipulator which bending controls the bending portion 12 as the tube body having movable bodies by rotationally driving the motor 23 through the motor driver 43 based on a command signal by an operation command by a user.

In this case, the FPGA block 36 comprises an estimation section 36a which estimates (calculates) a load value to the motor 23 as a disturbance estimation value (estimation value) using a manner of a disturbance observer, and a storage section 36b which memorizes (stores) periodical correction information in advance which depends on mesh positions of gears constituting a reduction gear unit, in order to perform calculation of the load value precisely. More specifically, a description will be made later referring to (LUT73 in) FIG. 9.

Figure 3:
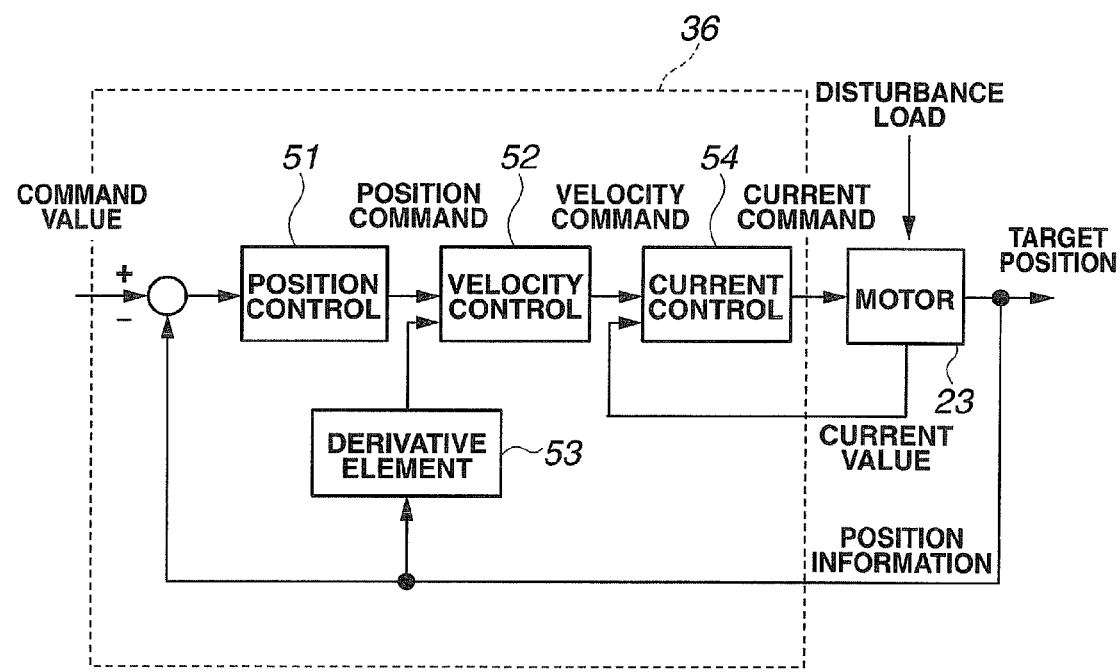
FIG. 3 is a signal flow diagram of a motor driving system in the motor unit.

FIG. 3 shows a signal flow chart of the motor driving system by the FPGA block 36. As shown in FIG. 3, a difference value obtained by subtracting the position information from the position information detecting means of the motor 23 from the command value based on the command signal from the operation commanding unit 4 is inputted to a position control block 51 of the FPGA block 36.

The position control block 51 outputs a position command generated from the difference value to a velocity control block 52. To the velocity control block 52, velocity information generated by differentiating the position information with a derivative element is also inputted. The velocity control block 52 outputs a velocity command which is generated from the position command and the velocity information to a current control block 54.

To the current control block 54, a value of a current flowing through the motor 23 is also inputted. Then, the current control block 54 provides a current command which is generated from the velocity command and the current value to the motor 23 as a drive power.

The motor 23 performs a rotational drive to a target position according to the current command and position information etc. in the drive is fed back to the motor driving system.

In this case, the motor 23 is actually connected to a load to bend the bending portion 12 through the planetary gear reduction mechanism 44, and the present embodiment employs the technique of disturbance observer which calculates the load, which is an estimated value (load value), as a disturbance load.

In this case, in addition to the usual bending drive control state, there may be a case where the distal end portion 11 of the bending portion abuts against body wall, etc. to deviate from the usual load state.

The present embodiment has a configuration comprising a determination function of determining a state deviated from the usual bending drive control state in addition to the usual bending drive control state by improving an estimation precision of the load value calculated by the technique of disturbance observer.

In the present embodiment, a manipulator of bending drive control is formed in which an external load for the motor 23 is regarded as a disturbance load and a value thereof is calculated and appropriate bending drive control is performed according to a calculation result thereof in dependence of an insertion state of the insertion portion 6. Thereby, it is enabled to perform an appropriate bending drive control without using a sensor.

FIG. 4 shows a block diagram for explaining a principle of estimating a load value by the above-mentioned disturbance observer. According to a current command from the motor driver 43, a command value u for torque which is proportional to a current value of the current command is applied to (an armature of) the motor 23 which is shown as a motor model block A by a dotted line in FIG. 4.

And a torque according to the torque command value u acts on the motor shaft. In this case, using Laplace operator s and assuming a motor torque constant is Kt, a torque of u·Kt acts on the motor shaft.

The motor 23 is driven at the number of revolutions per unit time (rotational velocity) in accordance with a motor moment of inertia J with respect to the torque exerted on the motor shaft. Using Laplace operator s, the rotational velocity is calculated (i.e. integral operation) by $1/(J \cdot s)$ and the motor position is calculated by a further integral operation ($1/s$) of the rotational velocity.

In the case of the actual motor 23, since a load is exerted on the motor shaft through the planetary gear reduction mechanism 44, a torque of a disturbance load d acts on the motor shaft to be reflected thereby.

A physical model block (or an operation processing block) which approximates (or simulates) elements of the motors 23 is arranged in parallel with respect to the motor model block A, as shown by a two-dot chain line 56.

However, the physical model block 56 is constituted by operation elements for calculating the disturbance load d. Specifically, in the motor model block A the disturbance load d is inputted to an adder, whereas the physical model block 56 is configured to be an operation block in which a subtraction block 59 estimates and outputs the disturbance load d. For this purpose, the command value u of torque is inputted to a first operation block 57 of a design motor torque constant Ktn (which approximates the motor torque constant Kt) in the physical model block 56.

Further, an operation output of the first operation block 57 is subtracted from output information of a second operation block 58, which performs an inverse operation to obtain a torque exerted on the motor shaft from the number of revolutions (rotational velocity) of the motor 23 (an operation of Jn·s using Laplace operator s), at the subtraction block 59, to calculate the disturbance estimated value da as an estimated value of the disturbance load d exerted on the motor shaft. Jn here denotes a design motor moment-of-inertia J which approximates a motor moment-of-inertia J of the motor 23.

In the calculation of the disturbance estimated value da as an observer output using the technique of disturbance observer of FIG. 4, since the planetary gear reduction mechanism 44 is connected to the motor shaft, the disturbance estimated value da is influenced thereby.

Figure 5A:
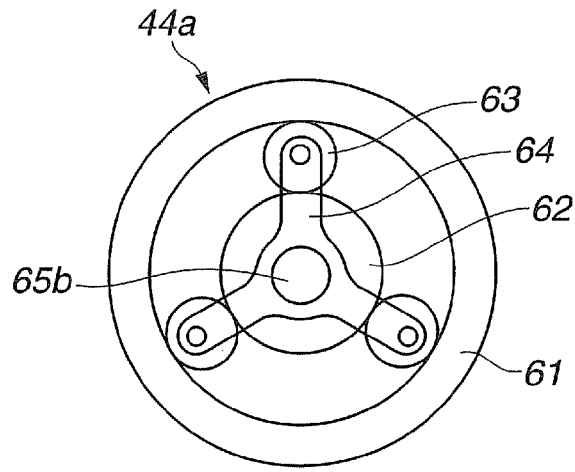
FIG. 5A is a front view showing a configuration example of a planetary gear used in the motor unit according to the embodiment.
Figure 5B:
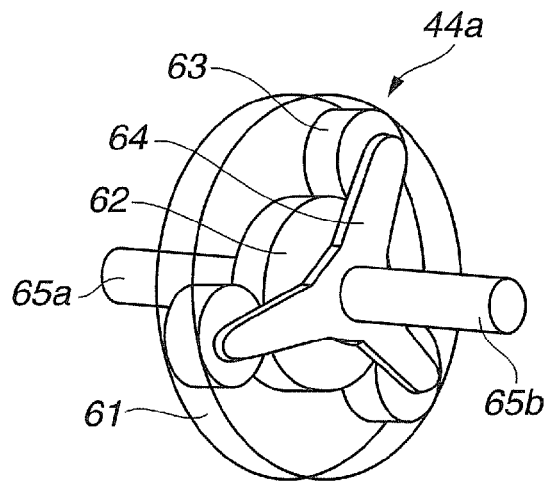
FIG. 5B is a perspective view showing the configuration example of the planetary gear used in the motor unit according to the embodiment.

FIG. 5A shows a perspective view viewed from front of one planetary gear 44a forming the planetary gear reduction mechanism 44, and FIG. 5B shows an oblique perspective view thereof.

The planetary gear 44a comprises an internal gear (which is also called as a ring gear) 61 having an outer side fixed and an inner circumference surface on which a gear is formed, a sun gear 62 arranged at a center of the internal gear 61, three planet gears 63, 63, 63 which revolve around the sun gear 21 while rotating on their respective axes, and an arm 64 holding these planet gears 63, 63, 63 to be respectively rotatable.

As shown in FIG. 5B, a rotation of a rotary shaft 65a on input side which is fixed to the sun gear 62 is reduced and a torque of the rotation is coaxially transmitted to a rotary shaft 65b on output side which is mounted on the arm 64 at the center thereof.

In the present embodiment, a plurality of planetary gears are successively connected with the planetary gear 44a as a unit to form the planetary gear reduction mechanism 44 which generates a torque capable of sufficiently bending driving the bending portion 12.

Figure 6:
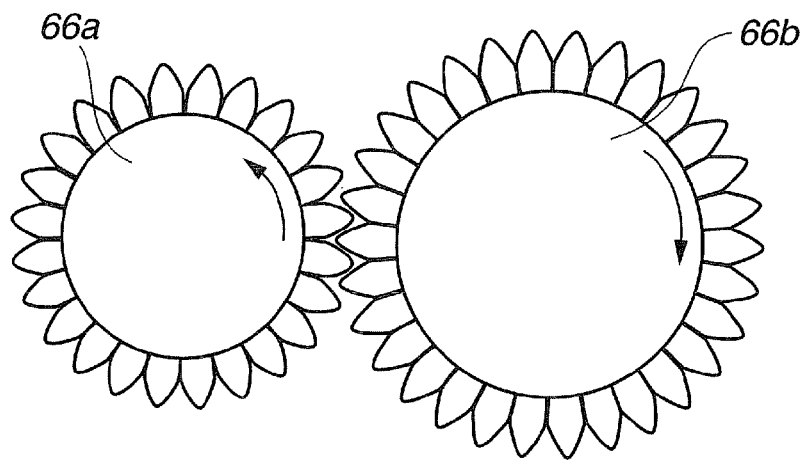
FIG. 6 is a diagram simplifying FIG. 5.

The planetary gear reduction mechanism 44 can be represented by two gears 66a, 66b which rotates in opposite directions as shown in FIG. 6 by simplifying and approximating the planetary gear reduction mechanism 44.

Note that the two gears 66a, 66b are shown as simple mechanical models of the drive gear 45 and the gear 47 in FIG. 2.

Figure 7:
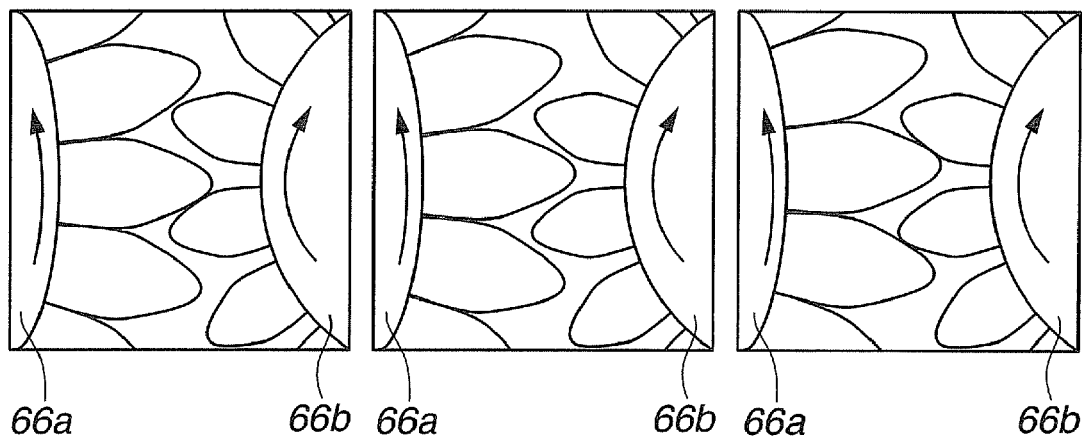
FIG. 7 is an explanatory diagram showing an example of meshing state in FIG. 6.

In this case, for example, three states occur as meshing states of the two gears 66a, 66b, as shown in FIG. 7.

Specifically, there arise a first state in which a rear periphery (with respect to a rotational direction) of a gear tooth, which is involved in meshing, of the gear 66a is in contact with a front periphery of a gear tooth, which is involved in meshing, of the gear 66b, as shown in the left side of FIG. 7, a second state in which the gear teeth of the two gears are out of mesh as shown in the center of FIG. 7, and a third state in which the respective two gear teeth of the gear 66a, 66b are in contact with each other.

In other words, the both gears 66a, 66b are not in an ideal state where the both gears meshes with each other completely, but there occurs a state where the gears are out of mesh with backlash. In the state where the both gears are completely in mesh with each other, when a state of one of the gears 66a, 66b is determined, the other of the gears 66a, 66b is univocally determined. However, in the case of the planetary gear reduction mechanism 44 of the present embodiment, a driving force transmission mechanism having backlash, which is generally shown in FIG. 7, is unavoidable.

Figure 8:
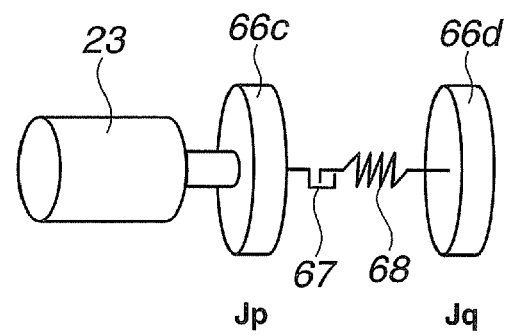
FIG. 8 is a diagram showing a typical model.

Then, the gears 66a, 66b as simplified in FIG. 6 can be approximated by a model as shown in FIG. 8 according to modeling by dynamical analogy.

As shown in FIG. 8, it is approximated by a model in which a gear 66c having a moment of inertia Jp and connected to the motor shaft of the motor 23 is connected to a gear 66d having a moment of inertia Jq through a friction pad 67 and a spring-damper 68.

As described later, in the case of the planetary gear reduction mechanism 44, although there are backlashes between the gears, the mechanism shows a periodical characteristic when the planetary gear reduction mechanism 44 is rotated since the gears constituting the planetary gear reduction mechanism 44 are formed to respectively have the predetermined number of gears.

Figure 10A:
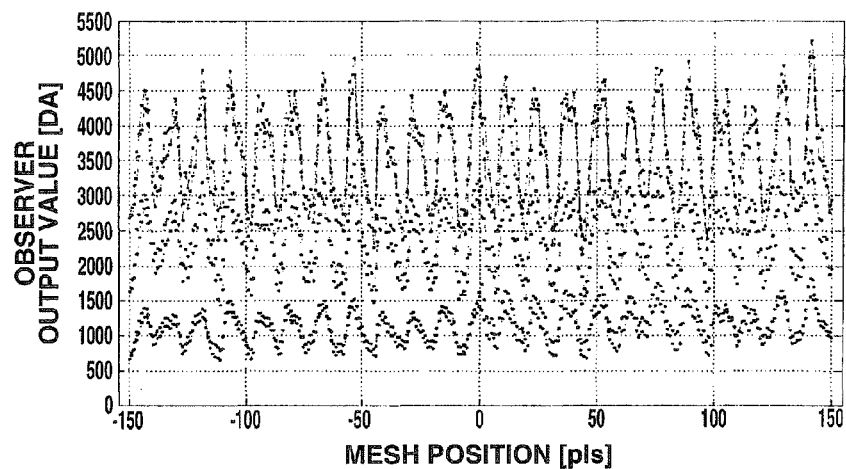
FIG. 10A is an explanatory diagram showing an observer output value for a mesh position of gears.

Further, actually, an observer output value as being observed varies in accordance with a mesh position of the drive gear 45 and the gear 47 shown in FIG. 2 (an example of observer output values with respect to the mesh position for respective load values (different load values) is shown in FIG. 10A).

And, the present embodiment is provided with a correction section 71 capable of reducing a precision decrease in a disturbance estimated value (the estimated value), the precision decrease being caused by the backlash between the gears and the mesh position of the gears in the planetary gear reduction mechanism 44, as shown in FIG. 9, i.e. capable of calculating a disturbance estimated value with high precision, using the technique of disturbance observer shown in FIG. 4. FIG. 9 shows configuration of a load calculation section 72 for calculating a load as a disturbance estimated value using the technique of disturbance observer.

As shown in FIG. 9, in the present embodiment, the load calculation section 72 is formed such that the disturbance estimated value da is further inputted into a correction section 71 in the configuration shown in FIG. 4, to have a function of performing correction by the correction section 71.

The configuration as shown in FIG. 4 is disclosed by a conventional example in Japanese Patent Laid-Open Publication No. 2007-185355. In the case of the conventional example, a disturbance estimated value da had low precision by the backlash between the gears constituting the reduction gear unit and the mesh positions between the gears. Contrary to this, the present embodiment comprises the correction section 71 which performs correction for the backlash between the gears constituting the reduction gear unit and correction using correction information which is reflective of characteristics for the mesh positions of the gears.

The correction section 71 has a lookup table (abbreviated as LUT) which outputs periodical correction information, data value in the form of a sinusoidal wave, for example, as corrected disturbance estimated value db, upon input of an observer output value before correction which is outputted from the subtraction block 59, i.e. the disturbance estimated value da, and a position data generator 74 which generates position data Pd corresponding to mesh position between the drive gear 45 and the gear 47 and outputs the position data to the LUT 73.

The position data generator 74 generates position data Pd of the mesh positions between the gears 45, 47 upon input of an output value of the encoder 41 which detects a position of the drive gear 45 (connected to the motor shaft from the rotational position information of the motor 23), and an output value of the potentiometer 42 which detects position information of the gear 47.

Further, in the LUT 73, as a result of research of the correlation between the output value of the observer which periodically varies up and down substantially and the mesh position between the gears constituting the reduction gear unit in advance, data values of the periodical correction information capable of well approximating a high correlation amount thereof are stored to be associated with the position data Pd of the mesh position.

Therefore, the LUT 73, upon input of both the data da and data Pd, outputs a corrected disturbance torque db in which an influence of the backlashes between the gears constituting the reduction gear unit is reduced and the dispersion is reduced to be reflective of the substantially periodical characteristic depending on the mesh position between the drive gear 45 and the gear 47 (i.e. a corrected disturbance torque db of high precision).

The present embodiment with the above configuration has the following effects. The observer output value (the disturbance estimated value da) calculated by the technique of disturbance observer as shown in FIG. 4 shows a periodical characteristic by the backlashes between the gears and the mesh positions, and varies up and down substantially.

Meanwhile, FIG. 10A shows a characteristic example of a plurality of output values which correspond to different mesh positions.

In contrast to the above, according to the present embodiment, periodical output data (stored in the LUT 73 in advance) which are approximately reflective of the characteristic which varies in dependence on the detected mesh position between the gears are read out in the correction section 71, as shown in FIG. 9.

Figure 10B:
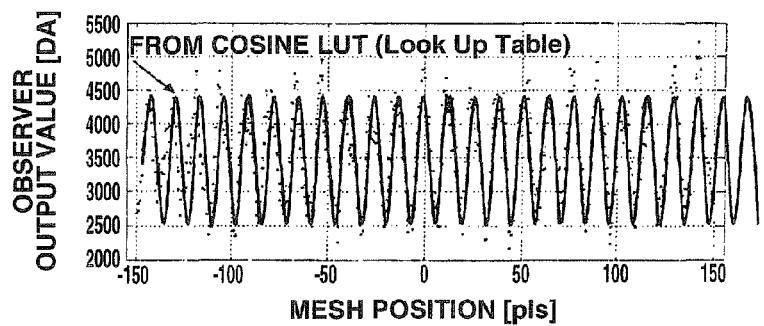
FIG. 10B is an explanatory diagram showing information of correlation between a gear position stored in a lookup table of a correction section in advance and the observer output value.
Figure 10C:
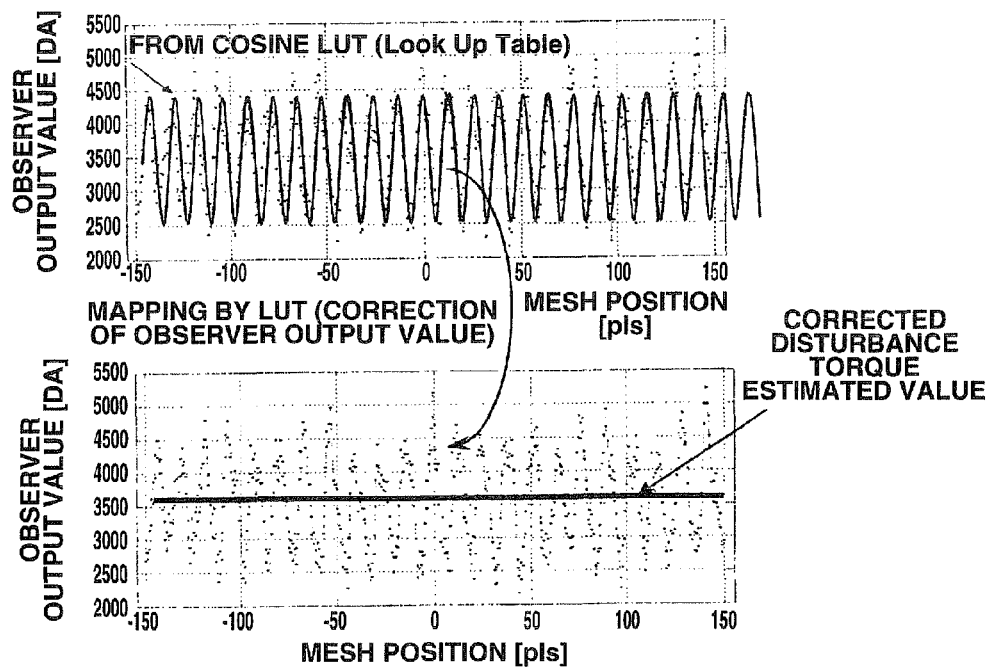
FIG. 10C is an explanatory diagram showing a disturbance torque estimated value after correction of the observer output value using information of FIG. 10B.
Figure 10D:
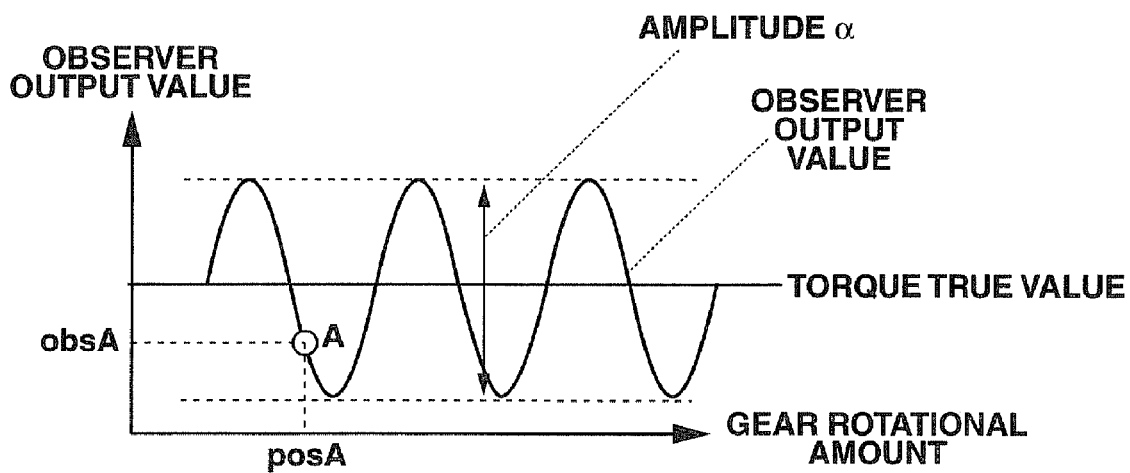
FIG. 10D is an explanatory diagram of calculating an observer corrected output value.

In the LUT 73, the correlation between the gear position and the observer output da is stored in advance, as shown in FIG. 10B. Specifically, relation between a gear meshing rotational amount (mesh position) and an observer output value da is allocated as a lookup table of a cosine function. This is because if time-series data of the observer output da are substituted by the cosine function, it can be extracted what part of the time-series data the observer output value da indicate, provided that the time information is known.

For example, it is assumed that an observer output value da at a point A is detected. The observer output da at A is outputted as a value obtained by multiplying an amplitude α/2 by cos(pos) with respect to a torque true value as a reference value. Actually, since an offset value β exists, extraction of the torque true value, i.e. a disturbance estimated value db as a corrected observer output value is realized by adding an amount of the offset value.

Accordingly, the disturbance estimated value db as the torque true value of the torque is extracted by calculating an observer corrected output value based on the observer output value da outputted at A according to the following equation.

Observer corrected output value=1/(α·cos(posA)/2)× observer output value+β

A disturbance estimated value db as the torque true vale can be extracted by setting an observer corrected output value with respect to an observer output value in advance in the LUT 73 using the above calculation equation.

Note that in FIG. 9, although it is configured that the observer output value da is inputted into the LUT 73, it may be configured that the observer output value da is not inputted into the LUT 73, but is subjected to subtraction or addition by the correction information to generate the disturbance estimated value db.

Figure 10E:
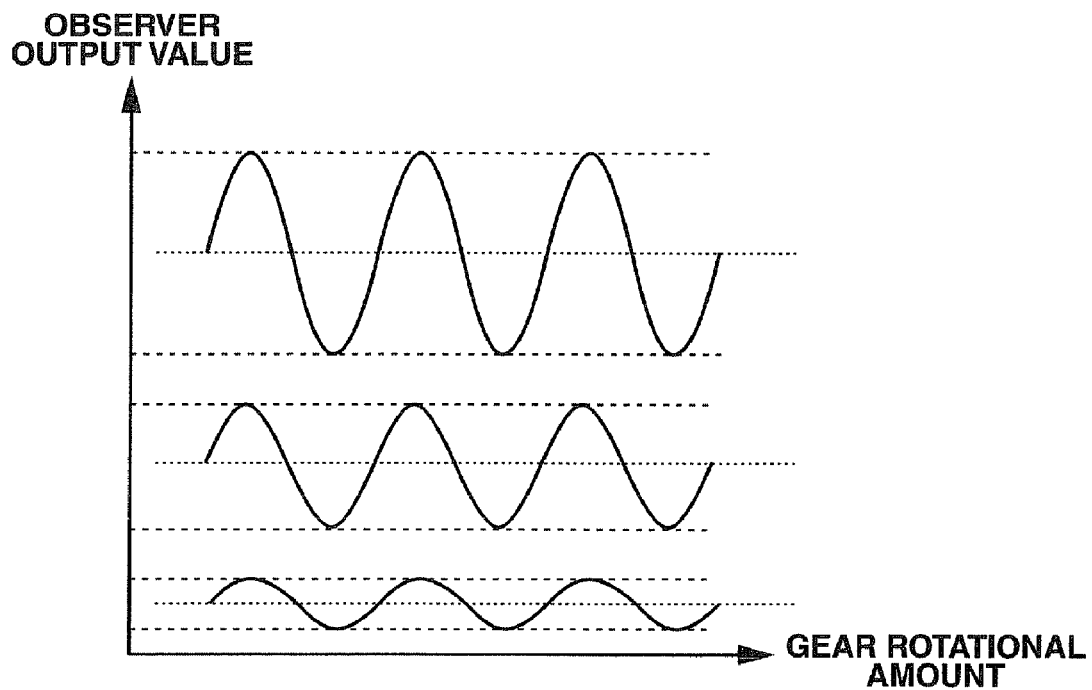
FIG. 10E is a diagram showing time-series data of FIG. 10A in a simplified manner.

Meanwhile, as shown in FIG. 10A, various torque amounts are actually applied as a disturbance torque as well as a constant torque. FIG. 10E is simplified representation of the time-series data of FIG. 10A. As shown in FIG. 10E, a peak value and an offset value of the observer output value tend to vary in accordance with the applied torque value. Generally, amplitude and also offset amount of the time-series data of the gear rotational amounts-observer output value da increase as the applied torque increases. Thus, detection of an arbitrary disturbance amount is made possible by setting an observer corrected value derived by the following equation where the amplitude is represented by α (obs) and the offset value is represented by a function of β (obs) and the observer output, in the LUT 73.

Observer corrected output value=1/(α(obs)·cos(posA)/2)×observer output value+β(obs)

As described above, by correcting the observer output value da using the information of mesh position of the gears, the disturbance estimated value db which actually represents precise approximation with reflection of the periodical characteristic in dependence of the mesh position can be calculated as an observer output value.

Further, a trigonometric function of cosine is used in the present embodiment, but a trigonometric function of sine may be adopted.

Thus, according to the present embodiment, a tension state in the bending drive control can be calculated with relatively high precision and therefore it is not required to provide a sensor in the insertion portion 6. Therefore, the endoscope 2 with the insertion portion 6 having a small diameter can be realized and an operation of an endoscope inspection by insertion of the insertion portion 6 into the body cavity. Accordingly, a manipulator realizing an electric bending control apparatus and an electric bending endoscope apparatus with improved operability such as insertion can be provided.

Further, an calculation result of an estimated value of the load calculated by the load calculation section is notified to a user such as an operator. Furthermore, from a judgment result C by a judging section 75 it can be confirmed whether it is in a normal bending drive control state or not, so that operability in performing the endoscope inspection by the operator can be improved.

Since the calculation result of the estimated value of the load is displayed on the endoscope monitor 5 as means for displaying the endoscope image, the operator can confirm the calculation result of the load in a state of observing the endoscope image.

(Modified Example of Embodiment 1)

Figure 10F:
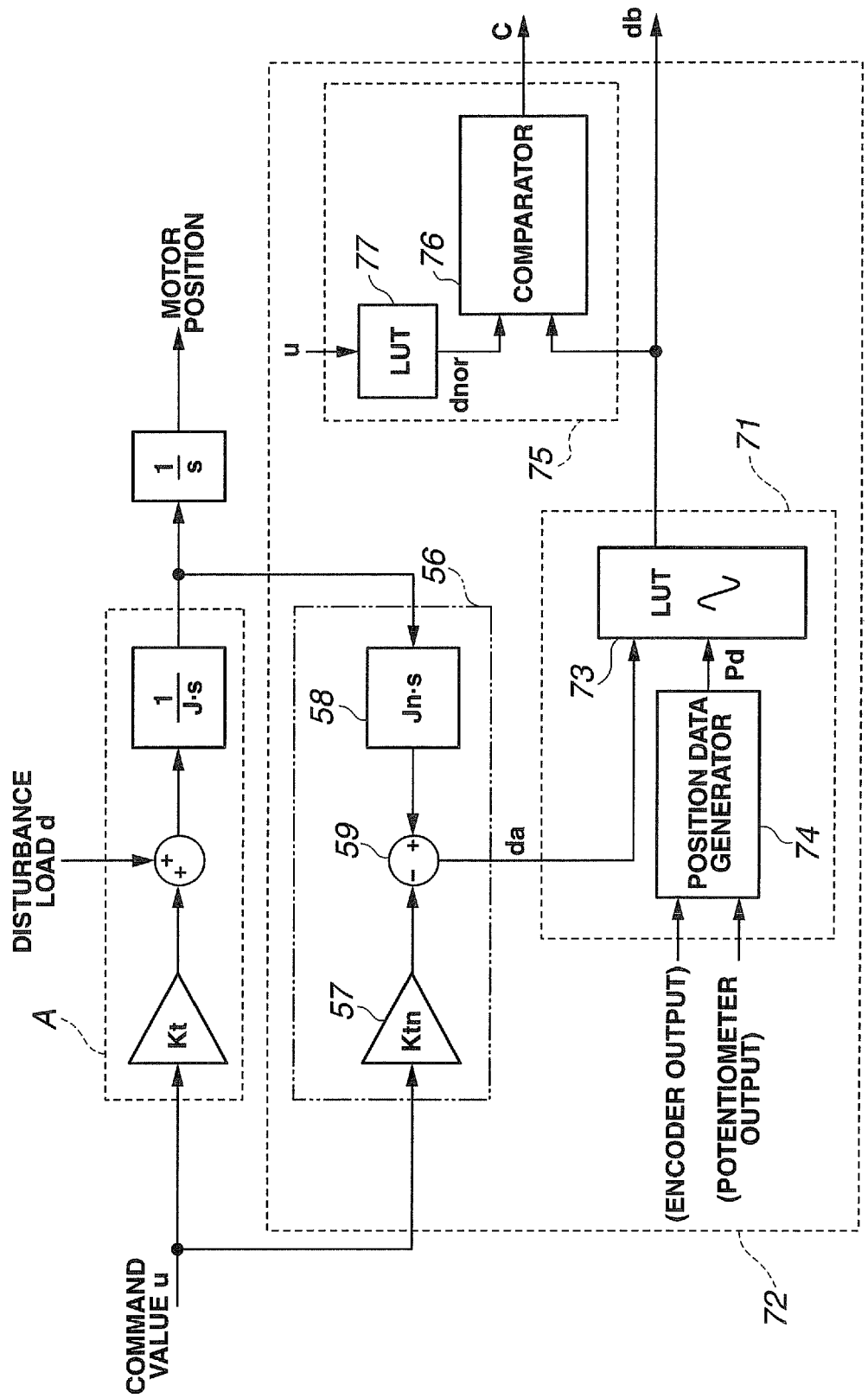
FIG. 10F is a block diagram showing a configuration of calculating a disturbance estimated value using the technique of disturbance observer in a modified example of the embodiment 1.

Further, as a modified example of the embodiment 1 shown in FIG. 9, it is made possible to perform judgment of the load by a configuration as shown in FIG. 10F.

In FIG. 10F, a load judging section 75 is provided in the configuration of the embodiment 1 shown in FIG. 9. The modified example of FIG. 10F comprises the judging section 75 which performs a judgment whether the disturbance estimated value db is in the normal bending drive control state (abbreviated as normal state) or a restricted state where the bending is restricted with the distal end 11 being in contact with body wall. In other words, the judging section 75 performs the judgment whether the estimated value of the load is in the normal state which corresponds the command value (drive command signal) based on the operation commanding unit 4 or in an external force acting state (restricted state) in which an external force deviated from the normal state is acting.

The judging section 75 comprises a window-type comparator 76 to which the disturbance estimation value db is inputted from the correction section 71, and a second LUT 77 which outputs a reference disturbance estimated value dnor in the normal state corresponding to the data of the command value u to the comparator 76 upon input of the data. Since the window-type comparator 76 compares two sets of data (in this example, the disturbance observer output db and the reference disturbance estimated value dnor) as time-series data, the window-type comparator 76 is formed as a correlation filter, not for determination based on whether or not all of the two sets of data coincide with each other, but for determining whether there is correlation between the two data series.

In the second LUT 77, information of the corresponding reference disturbance estimated value dnor in the normal state is stored in advance to be associated with the data of the command value u, for example. Note that the information of the reference disturbance estimated value dnor may be stored to be associated with the data other than the data of the command value u.

Then, when the disturbance estimated value u calculated by the correction section 71 deviates from the reference disturbance estimated value dnor which is estimated in the normal state by an allowable value or more, the comparator 76 constituting the judging section 75 outputs information of the judgment result C to the control unit 25 through the communication system block 34.

The control unit 25 receives the judgment result C and outputs judgment result information to also display the information of the judgment result C in the load value display area 5b, for example, to the image signal generating unit 16. Then, the judgment result information is notified to the user, e.g. by display.

For example, in the case of the judgment result C indicating judgment that the disturbance estimated value db calculated by the correction section 71 is equal to or greater than the value permissive from the reference disturbance estimated value dnor which is estimated in the normal state, a display or notification of a possibility of state in which the bending is restricted (with the bending portion 12 or the distal end 11 being in contact with body wall) is performed.

It may be configured that the result serves as means for providing information to the presentation of the force sense. It is also possible to make the endoscope to present the load by issuing the disturbance observer output db as it is to the force sense presenting means.

(Embodiment 2)

Figure 11:
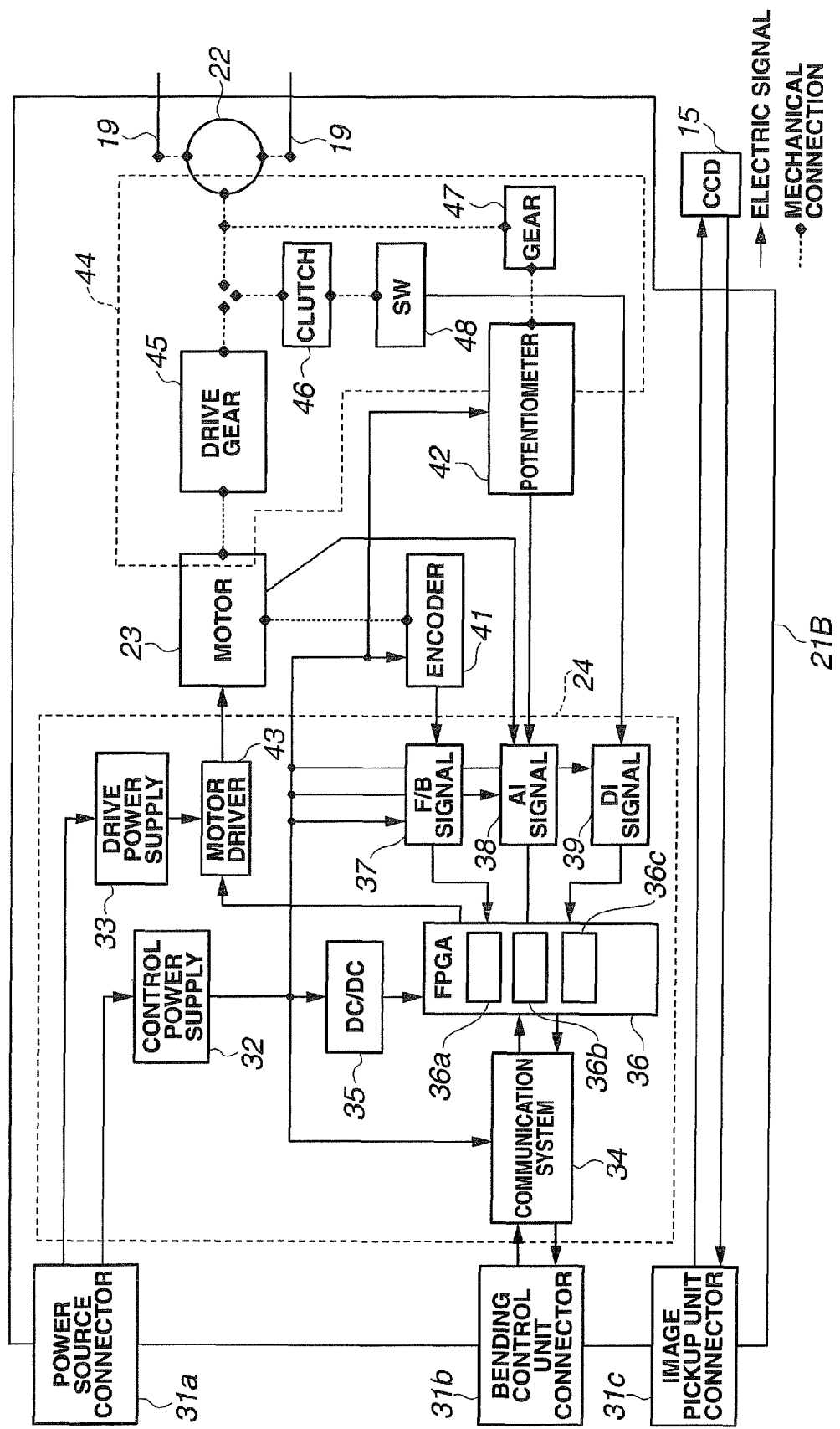
FIG. 11 is a block diagram showing a configuration of a motor unit according to embodiment 2 of the present invention.
Figure 12:
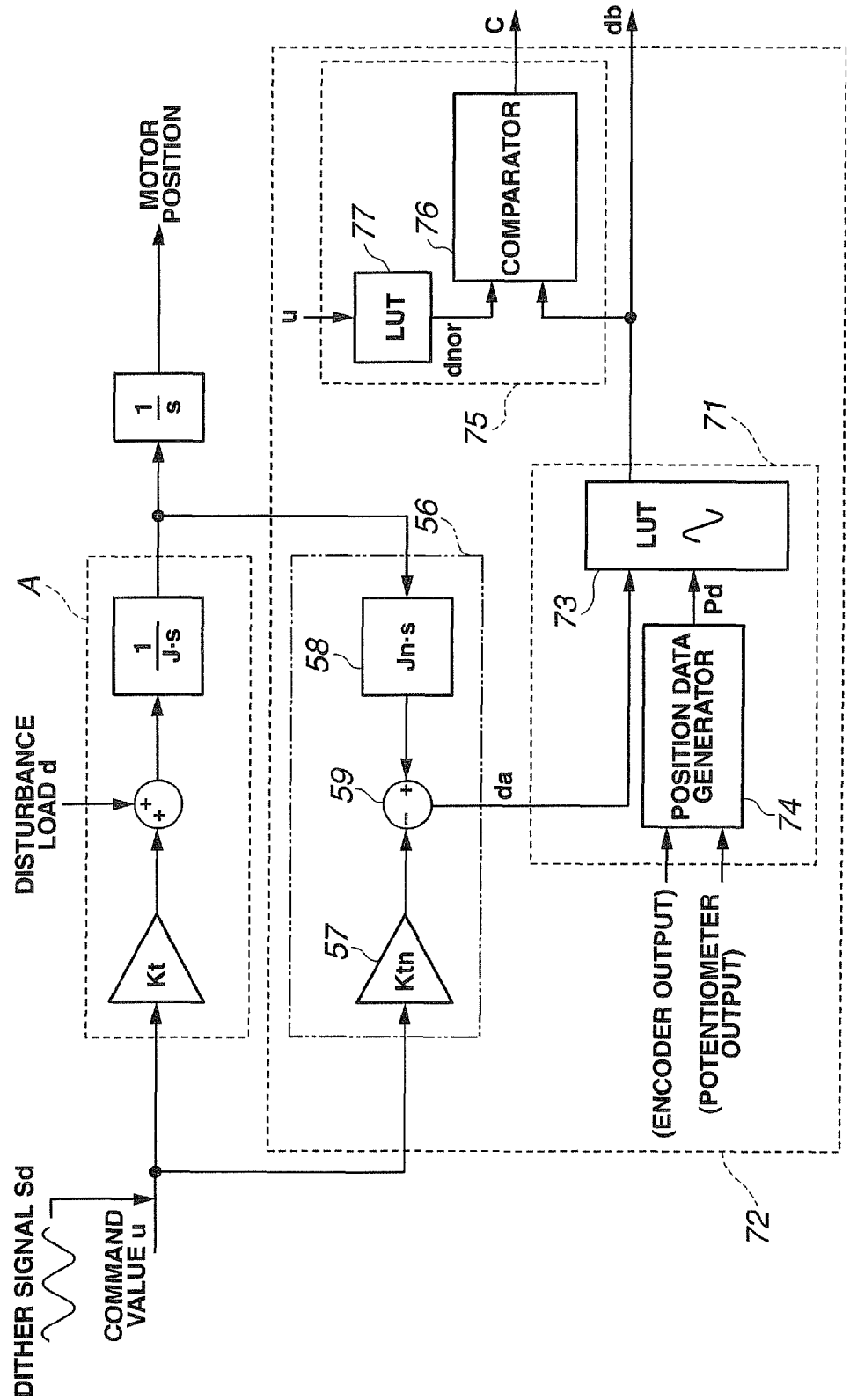
FIG. 12 is a block diagram showing a configuration of calculating a disturbance estimated value using a technique of disturbance observer in the embodiment 2.
Figure 13A:
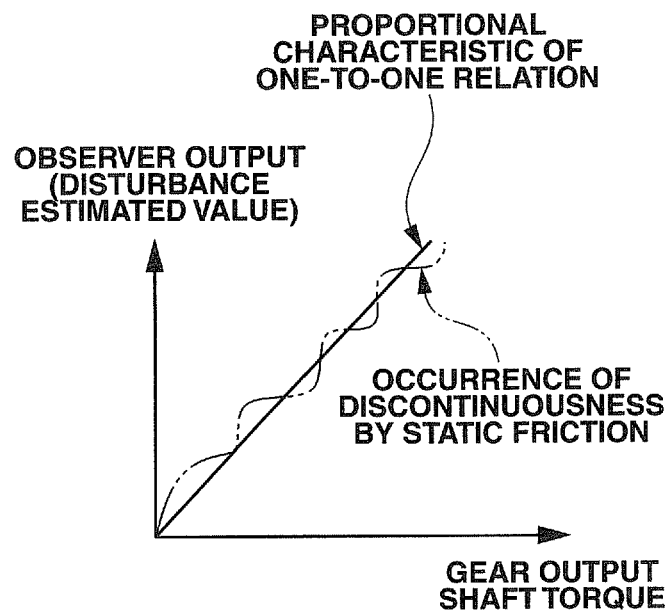
FIG. 13A is an operation explanatory diagram of the embodiment 2.

Next, embodiment 2 of the present invention will be described referring to FIG. 11 through FIG. 13B. FIG. 11 shows a configuration of a motor unit according to the embodiment 2 of the present invention, FIG. 12 shows a configuration of a load calculation section for calculating a disturbance estimated value using a manner of a disturbance observer, FIG. 13A shows an operation explanatory diagram of the present embodiment, FIG. 13B shows a diagram of actual relation of an observer output with respect to a disturbance torque.

Figure 13B:
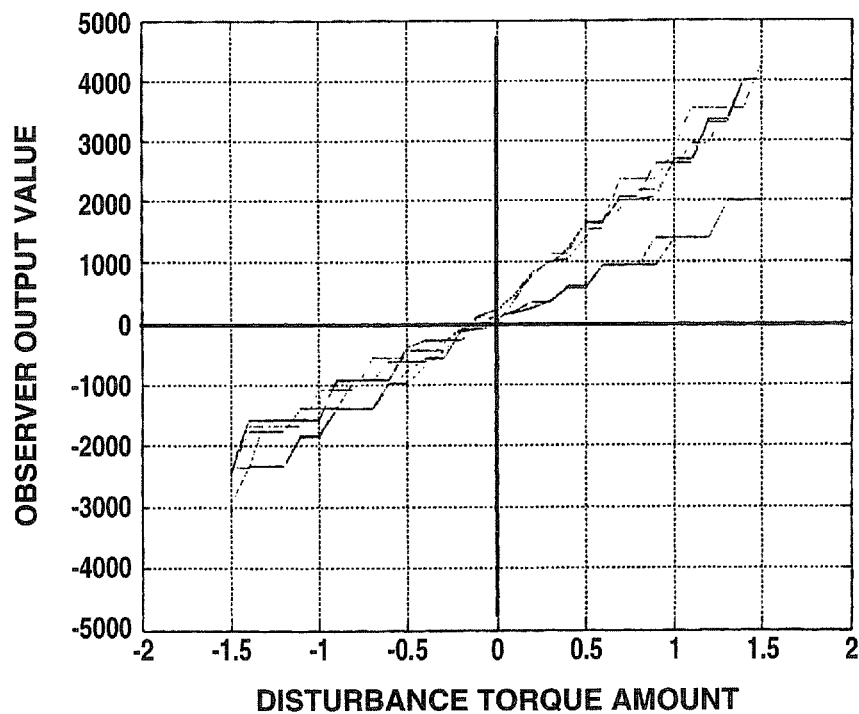
FIG. 13B is a diagram showing an example of dispersion of the observer output value with respect to the disturbance torque.

As shown in FIG. 13B, there arises dispersion in the disturbance observer output with respect to the applied disturbance torque, even to have a stepwise waveform. This is because an influence of static friction is dominant. Therefore, the present embodiment reduces the influence of the static friction between the gears constituting the reduction gear unit in the embodiment 1.

As shown in FIG. 11, a motor unit 21B of the present embodiment is configured such that the FPGA block 36, for example, in the motor unit 21 in FIG. 2 has a dither signal generator 36c which generates a dither signal as a vibration signal having amplitude to eliminate the static friction.

Then, the FPGA block 36 outputs the dither signal to a motor driver 43. Therefore, when an instruction signal to output the command value u is outputted from the FPGA block 36 to the motor driver 43, the instruction signal is outputted with the dither signal superposed thereon. Namely, it is configured that, when the command value u is applied to the motor 23, the motor is already in a state where the dither signal is applied thereto to be superposed (as vibration signal component).

In addition, the dither signal may be always applied to the motor driver 43. Alternatively, it may be restricted to a period in which the bending portion 12 is made bendable in the state where the drive gear 45 and the gear 47 is connected (specifically, ON/OFF of application of the dither signal may be performed in response to the ON/OFF signal of the switch 48 corresponding to ON/OFF of the clutch 46).

The other configuration is the same as that of the embodiment 1. FIG. 12 shows configuration of the load calculation section 72 according to the present embodiment. The load calculation section 72 has the same configuration as shown in FIG. 9 in the embodiment 1.

However, it is configured that the command value u applied to the motor 23 is applied with the dither signal superposed thereon as shown in FIG. 12.

Next, an operation of the present embodiment will be described.

When the bending drive control of the bending portion 12 is performed by the motor 23 through the planetary gear reduction mechanism 44 as the reduction gear unit, a value of a friction coefficient in the driving varies in dependence on whether the gears constituting the planetary gear reduction mechanism 44 are in a static state or in a dynamic state.

Therefore, precision of the observer output value as the calculated disturbance estimated value decreases due to an influence of whether the gears in the actual driving are in a static friction state or in a dynamic friction state. A schematic characteristic example of lowering of precision of the observer output value which is actually observed is shown by the two-dot chain line in FIG. 13.

Due to the influence of the static friction, the observer output actually observed is not in one-to-one relation with respect to the gear output shaft torque, but has a characteristic of a relation having width or a discontinuous relation with respect to the gear output shaft torque. Accordingly, in estimating the observer output value, the precision thereof decreases.

In contrast, in the present embodiment, at least when driving the bending portion 12, it is configured that the dither signal Sd as vibration signal is applied to the motor 23 so as to maintain the dynamic friction state (in other words, eliminate the static friction state).

For this purpose, in a state where the operator is able to perform the bending with the clutch 46 turned into the connection state, a vibrational torque of small amplitude is applied to the drive gear 45 and the gear 47, so that the dynamic friction state is maintained.

Thus, as seen from a characteristic diagram shown by the solid line in FIG. 13A, the influence of the static friction is eliminated, and it can be improved to have a characteristic corresponding to the one-to-one relation (ideally) in the case of the dynamic friction state only. In actually driving the bending portion 12, at least the dynamic friction state can be maintained, and therefore a disturbance estimated value db of high precision can be acquired by eliminating the influence of the static friction.

As described, according to the present embodiment, since at least when driving the bending portion, it is configured that the gears constituting the reduction gear unit are driven in the dynamic friction state, the influence of the static friction is eliminated and, in addition to the effects of the embodiment 1, more accurate calculation of the load is made possible.

Besides the above effect, the present embodiment has the same effects as the embodiment 1.

(Embodiment 3)

Next, embodiment 3 of the present invention will be described referring to FIG. 14 through FIG. 17.

Figure 15:
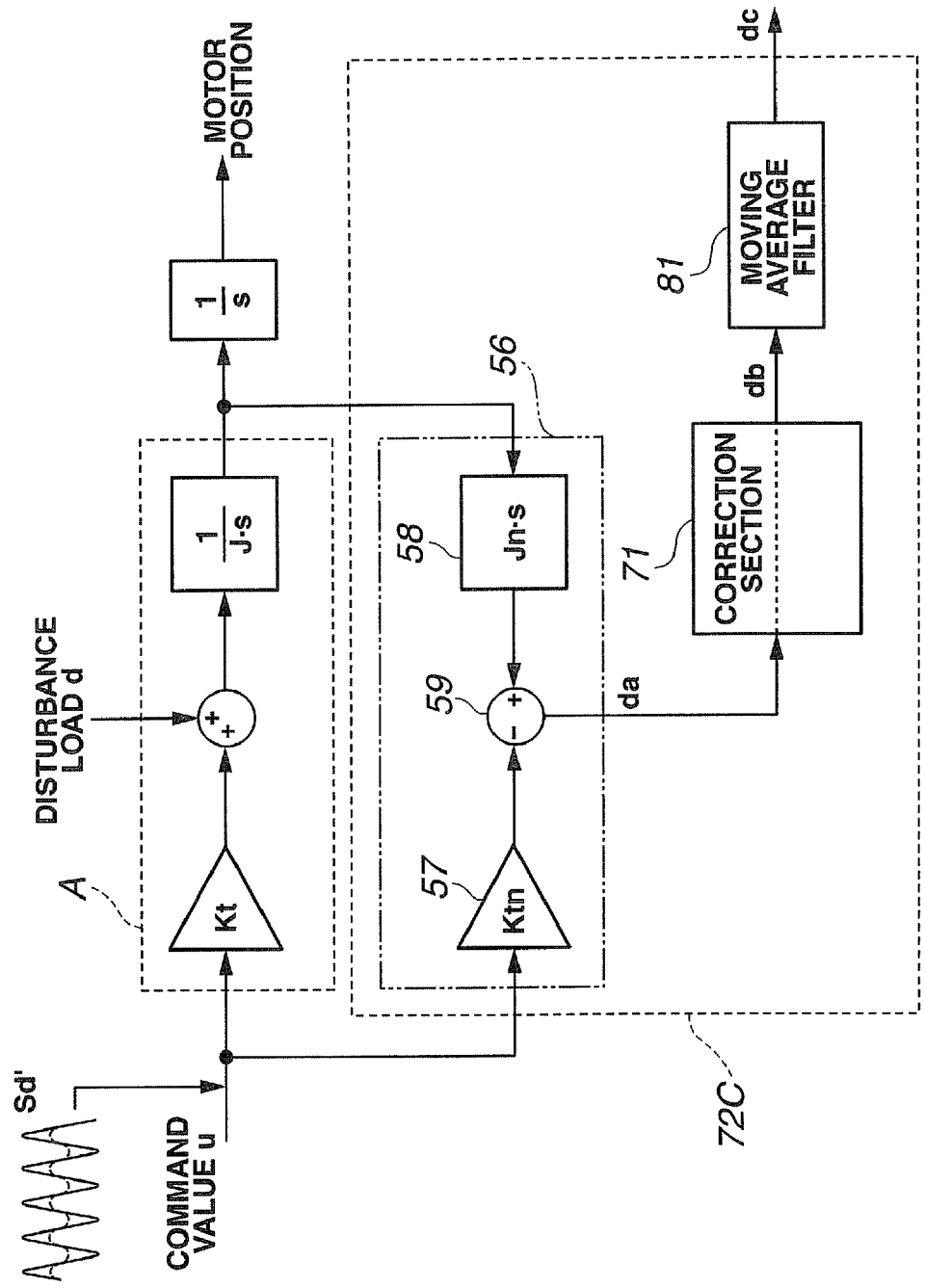
FIG. 15 is a block diagram showing a configuration of calculating a disturbance estimated value using a technique of disturbance observer in the embodiment 3.
Figure 16:
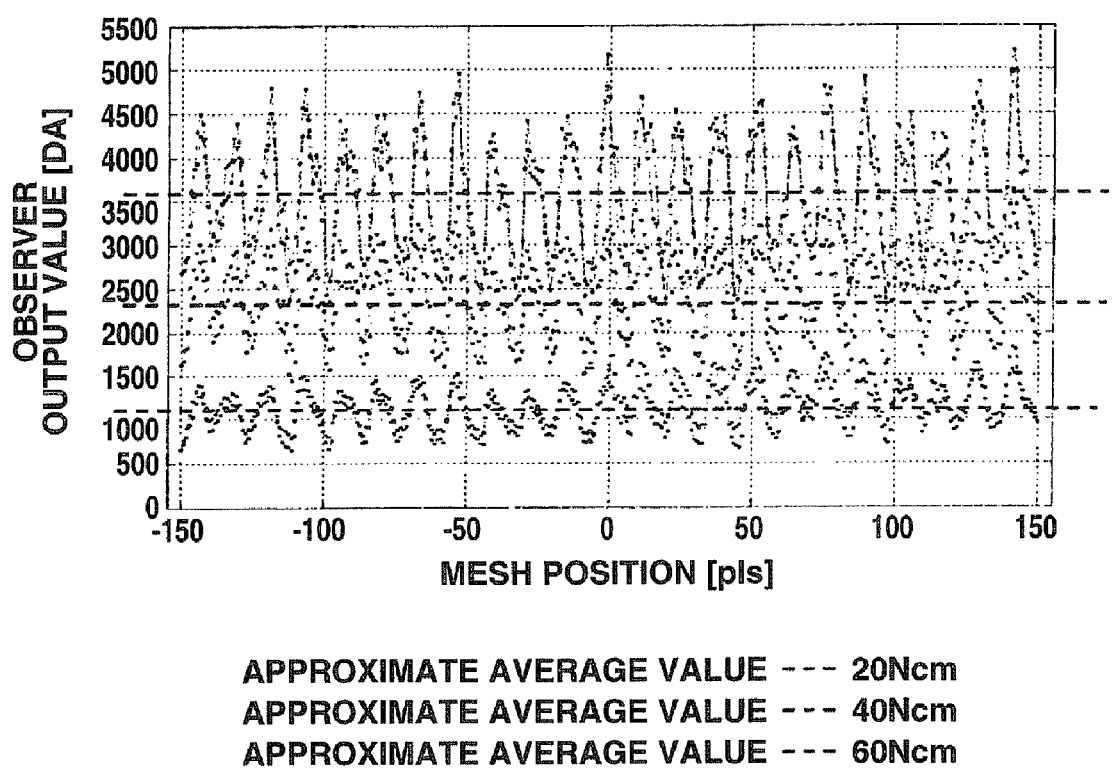
FIG. 16 is a diagram showing relation between an example of characteristic of the observer output value and an average value of peak and trough values of the observer output values with respect to a mesh position observed in static state.
Figure 17:
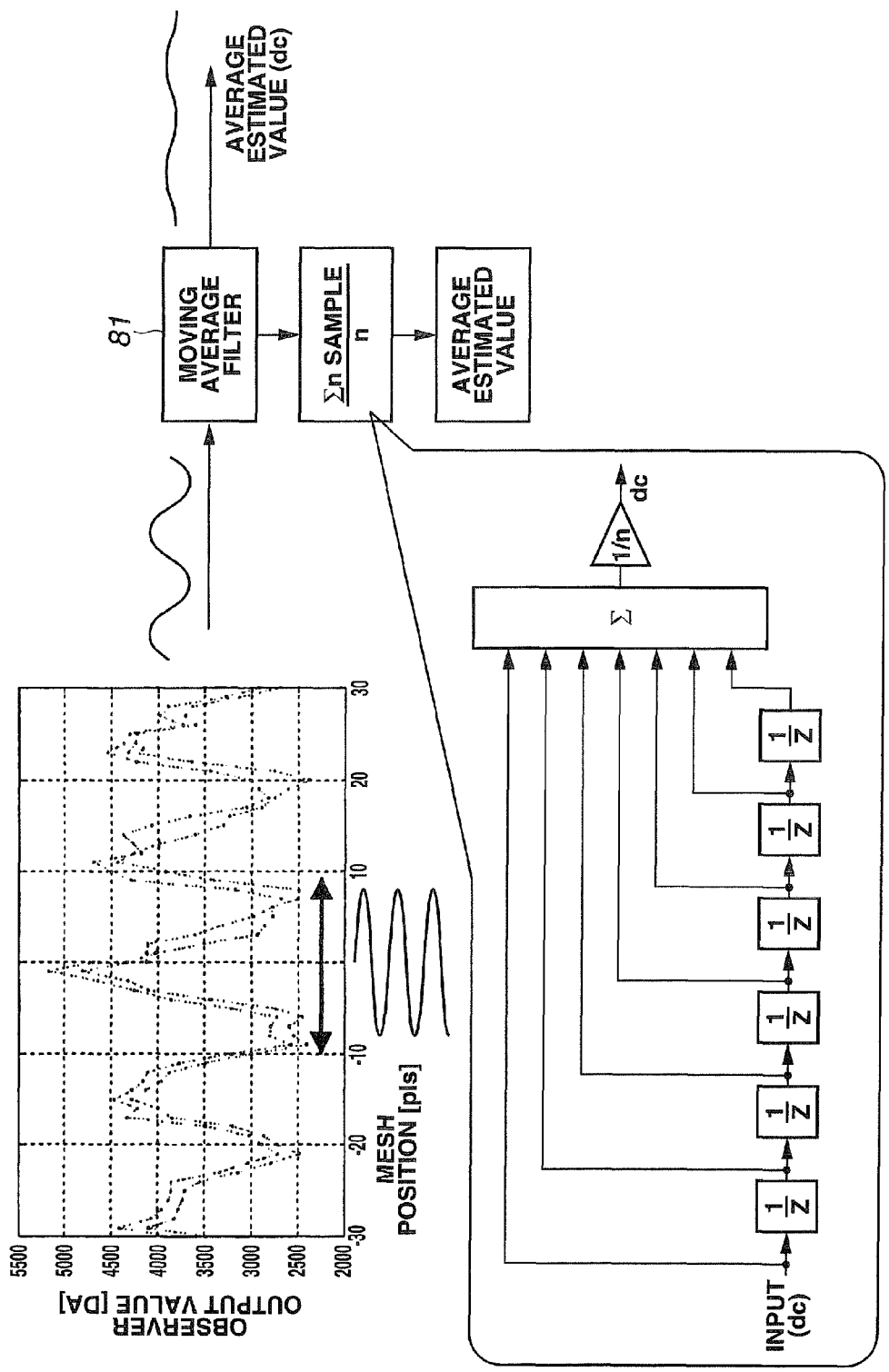
FIG. 17 is an operation explanatory diagram of the embodiment 3.

FIG. 14 shows a configuration of a motor unit according to the present embodiment, FIG. 15 shows a configuration of a load calculation section, FIG. 16 shows relation between an example of characteristic of the observer output value and an average value of peak and trough values of the observer output values with respect to a mesh position observed in a static state, and FIG. 17 shows an operation explanatory diagram of the embodiment 3.

As shown in FIG. 14, a motor unit 21C according to the present embodiment has the dither signal generator 36c as the generating means of vibration signal as the embodiment 2 has in the configuration of the embodiment 1. In the present embodiment, the FPGA block 36 comprises an adjustor (or a setting section) 36d so as to output a dither signal Sd with amplitude adjusted as described bellow. Further, the present embodiment calculates the disturbance estimated value with high precision in a period of a drive stopping state or a static state in which the command value u is not applied to the motor 23.

FIG. 15 shows a configuration of the load calculation section 72C in the present embodiment.

Additionally, in the present embodiment, a moving average filter 81 which calculates, from an output of the correction section 71 as explained in the embodiment 1, a moving average thereof is provided, to form the load calculation section 72 C which renders the averaged estimated value outputted from the moving average filter 81 serving as the disturbance estimated value dc.

In addition, the present embodiment can be applied to a case of configuration in which an output of the subtraction block 59 is inputted into the moving average filter 81 without inputting into the correction section 71 as shown by the dotted line in FIG. 15. The other configuration is the same as the embodiment 1. Next, an operation of the present embodiment will be described.

In the above mentioned FIG. 10A, it is described that in calculating a load value by the disturbance observer, the observer output value as being observed has periodicity because of the backlash and mesh position of the gears, and the output value varies up and down substantially.

In contrast, by averaging peaks and troughs of the observer output values observed in applying a torque in the static state, the value obtained thereby is generally proportional to the actual average value in time in the case of the substantial up and down variation, as shown in FIG. 16.

Accordingly, in the present embodiment, in the static state where a command is not issued (i.e. the motor 23 is not driven), the dither signal Sd' is applied such that the observer output value goes and returns between the peaks and the troughs (provided that the static state is maintained by retaining an amplitude such that the load side is not moved) and the disturbance estimated value is calculated by calculating the average value in time.

The dither signal shown in FIG. 15 indicates that this signal is applied to the motor 23 such as to oscillate between the peaks and the troughs.

As described, in the stopped state where the command value u is not issued, the dither signal Sd' is applied to the motor 23 such that the amplitude varies to the extent of not moving the load (the endoscope driving unit), and time aver-age of the output value is performed with respect to the observer output value in the application by the moving average filter 81.

FIG. 17 shows processing contents of the moving average filter 81 and an operation explanatory diagram thereof.

As shown in the left side of FIG. 17, the dither signal Sd' is applied to the motor 23 in a cycle such as to oscillate between the peak and the trough of the observer output value. In this case, the disturbance estimated value (observer output value) outputted from the correction section 71 is inputted into the moving average filter 81 shown in the right side of FIG. 17. As shown in the balloon frame, the moving average filter 81, using the disturbance estimated value db (outputted from the correction section 71) as an input signal, adds (integrates) a plurality of values obtained by sampling with a delay by a predetermined sampling period by an adder Σ and divides the sum by the number n as the number of samples to obtain an average estimated value as an output value of the moving average filter 81 to be outputted as a disturbance estimated value dc.

Note that 1/z in FIG. 17 shows a symbol of delaying an input signal by one sampling period. An averaged estimated value in the sampling periods of the plurality of numbers n is outputted for every sampling period while moving in time.

In this case, it is set that a product of one sampling period and the plurality of numbers n approximately coincides with a cycle of the peak and the trough.

With the above configuration, even in a static state where an command value u is not outputted, the load value in the state can be calculated accurately.

In addition, it is not limited to the case where the average value is calculated on the basis of the periods of the observer output values, the averaging may be performed on the basis of appropriate time periods.

Further, it may be configured such that the embodiment 2 and the embodiment 3 are combined. For example, in the static state where the command value u is not outputted, the bending portion 9 is bending-drive controlled in the manner of the embodiment 3, and for a time period in which the command value u is outputted, the bending drive control is switched to the manner of the embodiment 2.

Figure 18:
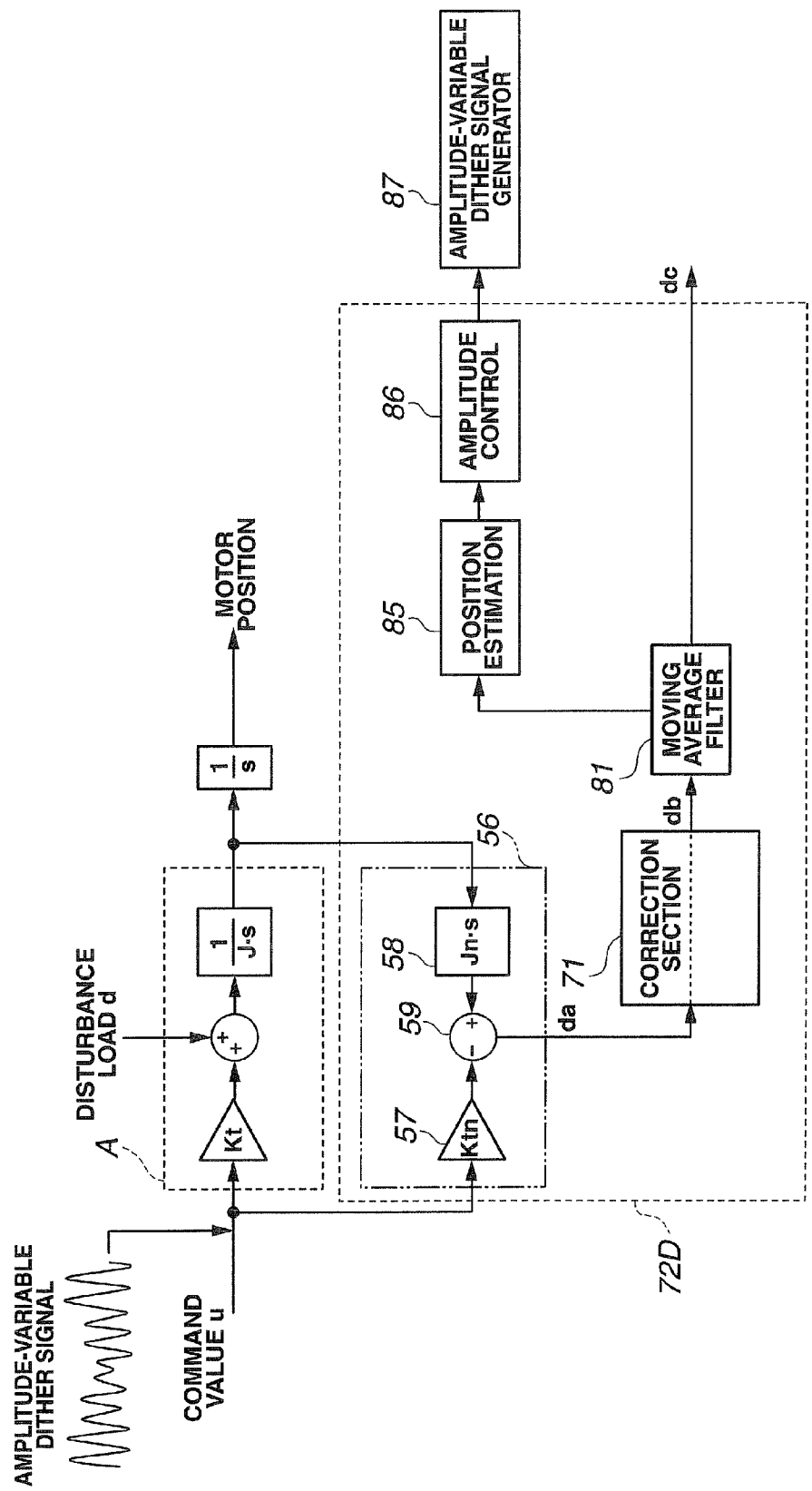
FIG. 18 is a block diagram showing a configuration of calculating a disturbance estimated value using a technique of disturbance observer in a modified example of the embodiment 3.

Next, a modified example of the present embodiment will be described. FIG. 18 shows a block diagram of a load calculation section 72D in the modified embodiment.

The present modified example is provided with a position estimation circuit 85 which estimates a phase position in a present cycle of cycles of the peaks and the troughs from data in the midst in the moving average filter 81 (e.g. form an adder), and an amplitude control circuit 86 which controls an amplitude of a dither signal based on an output of the position estimation circuit 85 in the configuration of FIG. 15.

Then, an amplitude command signal from the amplitude control circuit 86 is applied to an amplitude variable dither signal generating circuit 87, so that an amplitude of the dither signal in the vicinity of extreme values of peaks and troughs is controlled to be reduced.

Thus, in the present modified example, an amplitude of a dither signal of the amplitude variable dither signal generating circuit 87 is variably controlled by the amplitude command signal.

In addition, the amplitude variable dither signal generating circuit 87 may be provided in the load calculation section 72D. The other configuration is the same as the embodiment 3.

Figure 19:
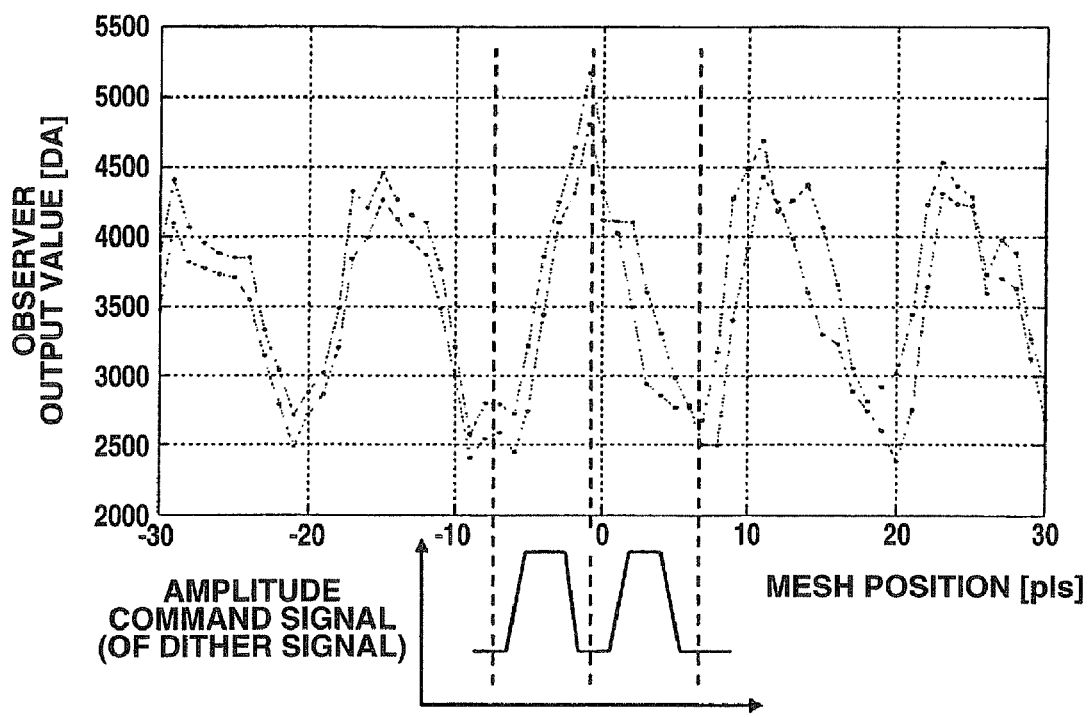
FIG. 19 is an operation explanatory diagram of the modified example.

FIG. 19 shows an example of the amplitude command signal from the amplitude control circuit 86 in the present modified example. As shown in FIG. 19, the amplitude command signal has a waveform in the form of an approximate pulse which has minimum amplitudes in the vicinity of phase positions where the observer output value is extreme and has amplitudes nearly maximum between these phase positions (in accordance with the position signals estimated by the position estimation circuit 85). Therefore, for example, a dither signal amplitude of the minimum required can be applied by setting to drive an arbitrary half cycle of the approximate pulse wave while detecting the approximate pulse wave.

By variably controlling the amplitude of the dither signal by the above amplitude command signal, the drive in the vicinity of the extreme values is suppressed.

Further, since the driving direction is changed to the opposite direction after one cycle with two extreme values passed, by suppressing the drive in the vicinity of the extreme values to the minimum, the change of driving direction can be performed smoothly and noises generated in driving the gears can be reduced. Besides these effects, the present modified example has the same effects as the embodiment 1.

(Embodiment 4)

Figure 20:
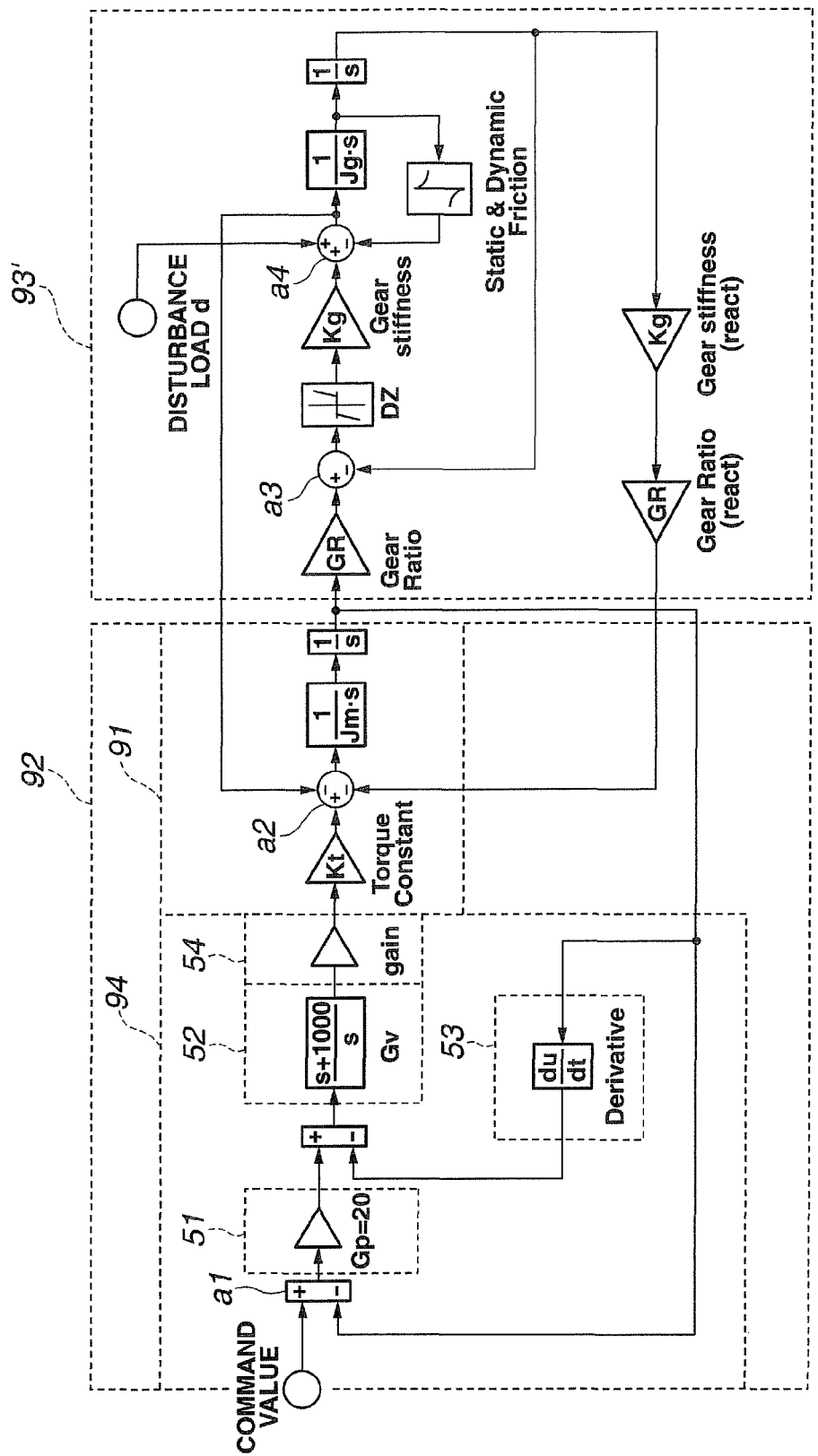
FIG. 20 is a block diagram showing a schematic configuration of a motor driving system in embodiment 4 of the present invention.
Figure 21:
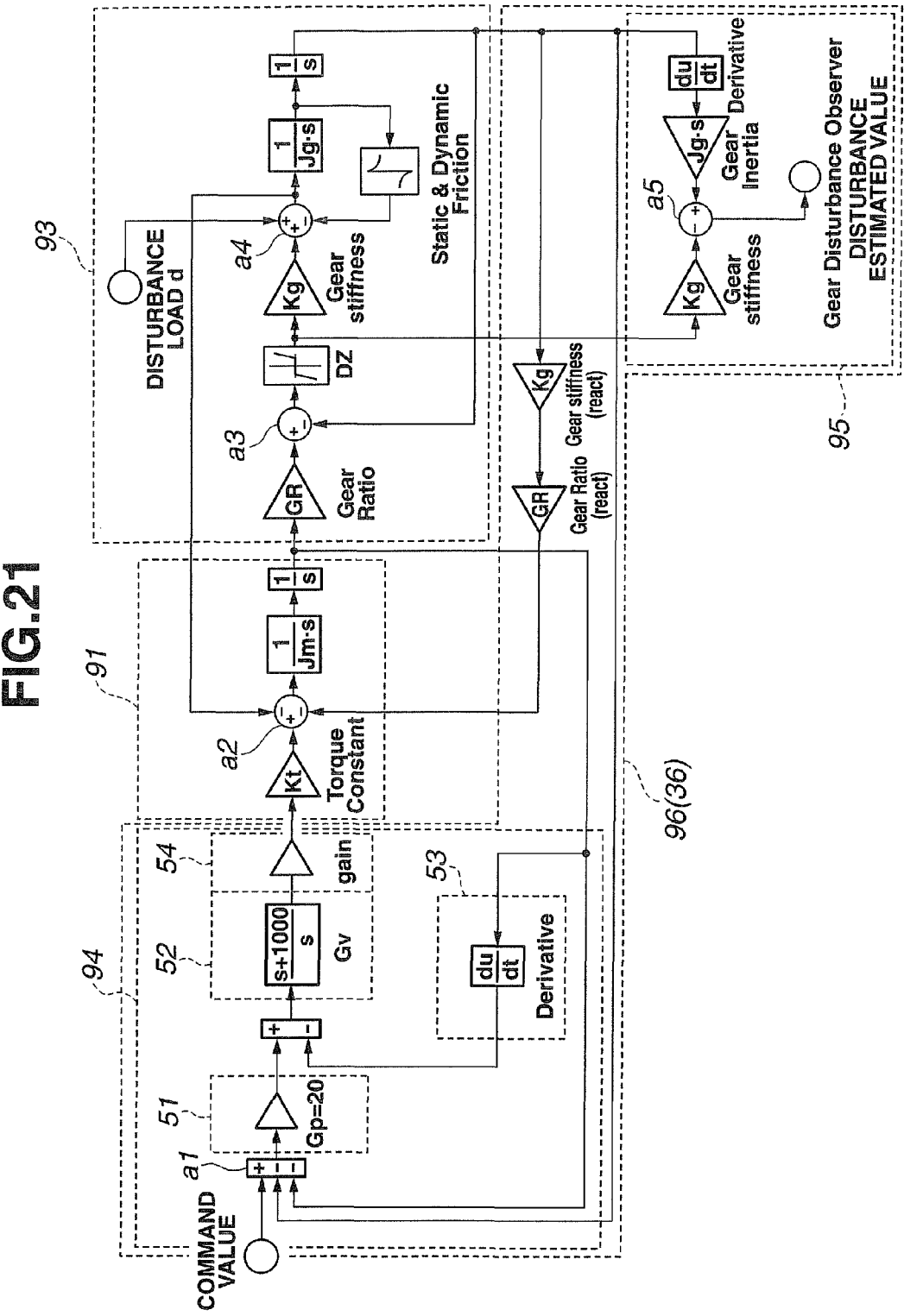
FIG. 21 is a block diagram showing a configuration of a motor driving system including a gear disturbance observer in the embodiment 4.

Next, embodiment 4 of the present invention will be described referring to FIGS. 20 and 21. FIG. 20 shows a schematic configuration of a motor driving system in the embodiment 4 of the present invention, and FIG. 21 shows a configuration of a motor driving system including a gear disturbance observer.

As described, the motor 23 is used with the planetary gear reduction mechanism 44, for example, as the reduction gear unit being connected thereto. A friction, a lost motion amount (dead zone), etc. are involved between a plurality of gears constituting the planetary gear reduction mechanism 44. In the above described embodiment, it is configured that a disturbance estimated value is calculated by adopting a motor model block A with an influence of friction, etc. (see FIG. 4, for example), using a (motor) physical model block 56 corresponding to the motor model block A by software and further performing correction by periodical correction information relating to mesh position by gears, etc.

A reaction from the endoscope side as the disturbance load d is applied to the motor side through the gears, and in the above described embodiments since the reaction is measured on the motor side, an influence of the gears is reduced by the correction of the measurement.

In contrast, the present embodiment uses models of a reduction gear unit or gear part constituting the reduction gear unit as well as a motor, and a model reflecting a substance of the gear part with much fidelity so that the disturbance load d is applied to the gear part. And, it is configured to be capable of calculating a disturbance estimated value of high precision without using the periodical correction information relating to the mesh position of the gears in the above described embodiments.

For this purpose, the present embodiment forms a motor model block and gear model blocks modeling the gear part such as the planetary gear reduction mechanism 44 including influences of the friction, the lost motion amount (dead zone), etc. and makes the disturbance load be applied to the side of the gear model blocks (to be configured to reflect a substance of the gear part with much fidelity).

And, it is configured that a gear physical model corresponding to the gear model block (specifically, a gear disturbance observer as a disturbance calculation section) is formed and the influence of friction, etc. is reduced by the physical model, so that the disturbance load d is estimated with high precision.

The configuration of the endoscope system and the motor unit according to the present embodiment is basically the same as that shown in FIG. 1 and FIG. 2. However, the motor unit driving system in FIG. 2 is modified to comprise a motor driving section 92 (including a motor section 91) and a gear section 93' as shown in FIG. 20.

The following equations of motion (1), (2) are given with respect to a gear model in which the gear is connected to the motor 23 as shown in FIG. 8.

$$Jm \cdot (d^2\theta m/dt^2) + r \cdot D \cdot \{(r \cdot (d\theta m/dt) - (d\theta_L/dt)\} + r \cdot K \cdot (r\theta m - \theta_L) = \tau \quad (1)$$

$$J_L \cdot (d^2\theta_L/dt^2) + F_L \cdot (d\theta_L/dt) + r \cdot D \cdot \{r \cdot (d\theta m/dt) - (d\theta_L/dt)\} + K \cdot (r\theta m - \theta_L) = 0 \quad (2)$$

$\theta m$, $\theta_L$ in (1), (2) denote an angle of the motor shaft, an angle of the gear shaft, respectively. $Jm$, $J_L$ represent the motor inertia (moment of inertia), the gear inertia taking the load into account, respectively. And, $r$, $D$, $K$, $\tau$, $F_L$ are a gear ratio, a viscosity constant, an elasticity constant, a motor torque constant, a gear static friction constant, respectively.

Based on the above equations of motion (1), (2), the actual motor driving section 92 and the gear section 93' are represented by the block diagram of FIG. 20.

And, it is configured to be capable of calculating a disturbance estimated value by adding a gear disturbance (estimation) observer 95 to the motor driving section 92 and the gear section 93' as shown in FIG. 21. Further, in this case, by utilizing the position information of the gear 47 detected by the potentiometer 42 (see FIG. 2) in the gear section 93', it is made possible to calculate a disturbance load with high precision.

In addition, a motor driving section 92 in FIG. 20 comprises a motor section 91 and a motor drive unit section 94 to drivingly control the motor section 91.

The motor drive unit section 94 has basically the same configuration as the component blocks (i.e. the position control block 51, the velocity control block 52, the derivative element 53, the current control block 54) in the signal flow chart as shown in FIG. 4.

And, the motor section 91 is basically the same as the motor model block A as shown in FIG. 4. While the motor model block A is defined excluding the integral operator (1/s) in FIG. 4, the motor section 91 is defined to include the integral operator (1/s) in the present embodiment since the position information is utilized in the present embodiment.

Further, FIG. 4 shows a simplified model configuration in which the disturbance load d is inputted into the motor section 91, whereas in the present embodiment, there is configured a model configuration more approximate to reality so that a disturbance torque d is inputted to the gear section 93' side.

Therefore, signal inputs into an adding point (addition point) after passing the torque constant Kt in FIG. 4 are different from those in FIG. 20.

At the addition point a2, a signal value taking into account reactions of a gear stiffness (Gear stiffness) and a gear ratio (Gear Ratio) with respect to the gear position information of the gear section 93' is added, and a signal, which is obtained by adding the disturbance load d exerted on the gear shaft at an addition point a4, is subtracted.

In addition, since an inertia (moment of inertia) of the motor is taken into consideration in the foregoing embodiments 1-3, the motor inertia is denoted by J, but, since a gear inertia is also taken into consideration, the motor inertia is denoted by Jm and the gear inertia is denoted by Jg in the present embodiment and the subsequent embodiments.

In FIG. 20, the gear section 93' is shown as a configuration including an actual gear model section and a section by software operation (specifically, the above mentioned reaction elements) by the FPGA block 36.

In contrast, in the more detailed configuration of the motor driving system of FIG. 21 in which the gear disturbance observer 95 is added, the actual gear model portion is denoted by numeral 93 and a portion by processing of software operation by the FPGA block 36 is shown by numeral 96 (36).

Namely, the FPGA block 36 has a configuration including the motor drive unit section 94, the gear reaction section and the gear disturbance observer 95 as shown in FIG. 20.

In FIG. 20 and FIG. 21, the motor position information of the motor section 91 is fed back to the addition point a1 and subtracted from a command value and then inputted into an operating element of a position control block 51.

Further, in the configuration shown in FIG. 21, the gear position information of the gear section 93 is additionally inputted into the addition point a1 and the control of the motor drive is performed based on a deviation value obtained by the subtractions with respect to the command value.

Namely, in the present embodiment, a motor control system is configured to be capable of reducing an error using the gear position information of the potentiometer 42 for detecting the position information of the gear 47 (see FIG. 2), to calculate a disturbance load by the configuration. As described, since the gear position information by the potentiometer 42 is utilized, even in a case where a gear disturbance observer 95 itself as the load calculation section having a simplified configuration is employed, it is enabled to calculate a gear disturbance estimated value with high precision.

Further, the position information of the gear 47 after passing through a gear ratio operation element is subtracted from the motor position information of the motor section 91 at the addition point a3. Then, the subtracted result, after passing through operation elements of a dead zone (DZ) such as backlash and looseness, a gear rigidity, is subjected to an addition of the disturbance load d thereto and a subtraction of a signal value obtained by operation of the static and dynamic frictions therefrom at the addition point a4.

The signal value obtained by addition at the addition point a4 is fed back to the addition point a2 and subjected to the subtraction as described, and undergoes the integral element (1/(Jg·s)), an integral element (1/s) to serve as gear position information to be detected by the potentiometer 42.

The gear position information is inputted into a derivative operation element du/dt of the gear disturbance observer 95. Then, in the gear disturbance observer 95, a disturbance estimated value is calculated by performing the operation processing which is the same as described referring to FIG. 4 (however, the motor is replaced with the gear).

Namely, the gear position information, the gear velocity information is calculated by the derivative operation element and further a value undergone by an inverse operation (Jg·s) of (1/(Jg·s)) of the gear section 93 side is inputted into the addition point a5. At this addition point a5, a torque taking account of a gear rigidity (Kg) with respect to a value containing the dead zone (DZ) (in the same manner as the gear section 93 side) is subtracted from the inputted value and the calculated disturbance estimated value is outputted from a disturbance output terminal.

Note that the gear inertia Jg, the gear rigidity Kg in the gear disturbance observer 95 are of design values (nominal values).

Further, the calculated disturbance estimated value is transmitted to the control unit 25 through communication block 34 as described in the embodiment 1, and notified by display, etc. in the endoscope monitor 5.

As described, in the present embodiment, since the gear position information detected by the potentiometer 42 is fed back to the command value to the motor 23 to utilize the position information positively, the influence of the friction, dead zone elements can be eliminated or reduced Further, since it is configured to directly detect the disturbance torque acting on the gear section 93 in the gear section 93, the load such as tension acting on the endoscope can be calculated with high precision without using a sensor.

Further, the calculated load value, etc. can be notified to a user such as operator by display.

(Embodiment 5)

Next, an embodiment 5 of the present invention will be described referring to FIG. 22 through FIG. 24. In the present embodiment, the disturbance load d is taken into account in the gear section in the same manner as the fourth embodiment, and further a concept of a state estimation observer is introduced to calculate the disturbance estimated value in the same manner.

For this purpose, a concept of a state estimation observer will be described first. In the state estimation observer, a state amount is estimated from information of input and output of the actual system using a virtual model for imitating the actual system.

State equations for the actual system and the virtual model are given as the following equations (3), (4).

$$\text{Actual system:} dx/dt = A \cdot x + B \cdot u \quad y = C \cdot x + D \cdot u \tag{3}$$

$$\text{Virtual model:} dxm/dt = A \cdot xm + B \cdot u \quad ym = C \cdot xm + D \cdot u \tag{4}$$

Here, A, B, C, D are coefficient matrix defining dynamics of the system, respective parameters in the actual system are the same as those in the virtual model, and the state variables x, xm and the output y, ym are different.

When a deviation e between the actual system and the virtual system is given as e=xm−x, $$\begin{aligned} de/dt &= dxm/dt - dx/dt \\ &= A \cdot xm - A \cdot x \\ &= A \cdot (xm - x) \\ &= A \cdot e \end{aligned} \tag{5}$$

Since the deviation converges when A is stable, converging time of state amount is controllable by providing a feedback mechanism between the actual system and the virtual model. When the output deviation is fed back to the model so that an error between the actual system and the virtual model is converged as soon as possible, the following equation is obtained, where L is a feedback gain.

$$\begin{aligned} dxm/dt &= A \cdot xm + B \cdot u - L \cdot (ym - y) \\ &= A \cdot xm + B \cdot u - L(C \cdot xm + D \cdot u - y) \\ &= (A - L \cdot C)xm + B \cdot u - L \cdot Du + L \cdot y \end{aligned} \tag{6}$$

A change of the deviation e in time is expressed as follows.

$$\begin{aligned} de/dt &= dxm/dt - dx/dt \\ &= (A - L \cdot C)xm + B \cdot u - L \cdot D \cdot u + \end{aligned} \tag{7}$$

-continued $$L \cdot (C \cdot x + D \cdot u) - (A \cdot x + B \cdot u)$$
$$= (A - L \cdot C)(xm - x)$$
$$= (A - L \cdot C)e$$

The deviation e is converged to A-LC.

As described above, the converging time is defined in dependence on the value of A-LC, and therefore, by setting the value of L such that the deviation e is converged as soon as possible, the state amount of the actual system and the state amount of the virtual model coincides with each other in real time, i.e. the value of the actual system can be estimated from the value of the virtual model.

Figure 22:
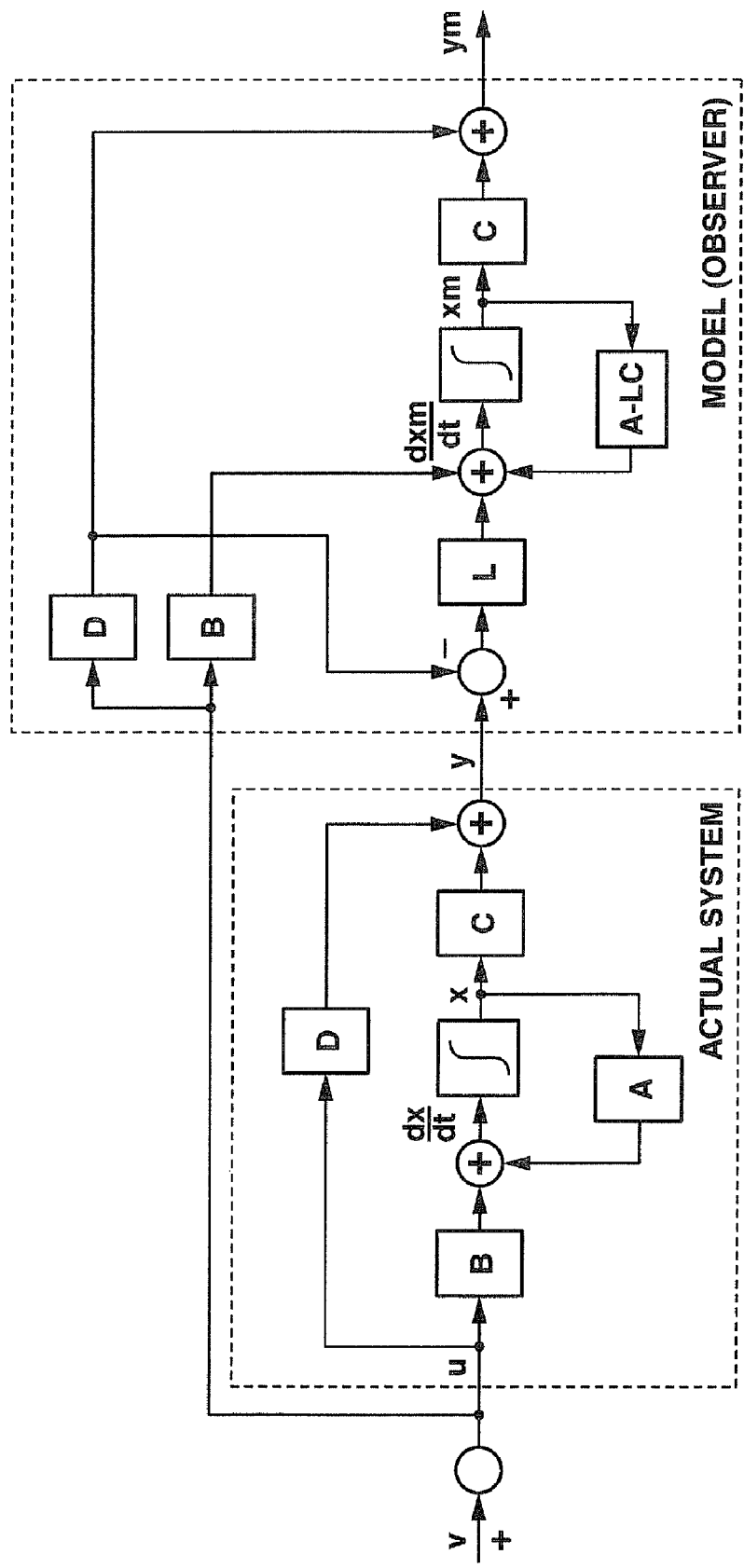
FIG. 22 is a block diagram showing relation between an actual system and a virtual model.

The relation between the two systems with feedbacks is shown by a block diagram of FIG. 22.

Figure 23:
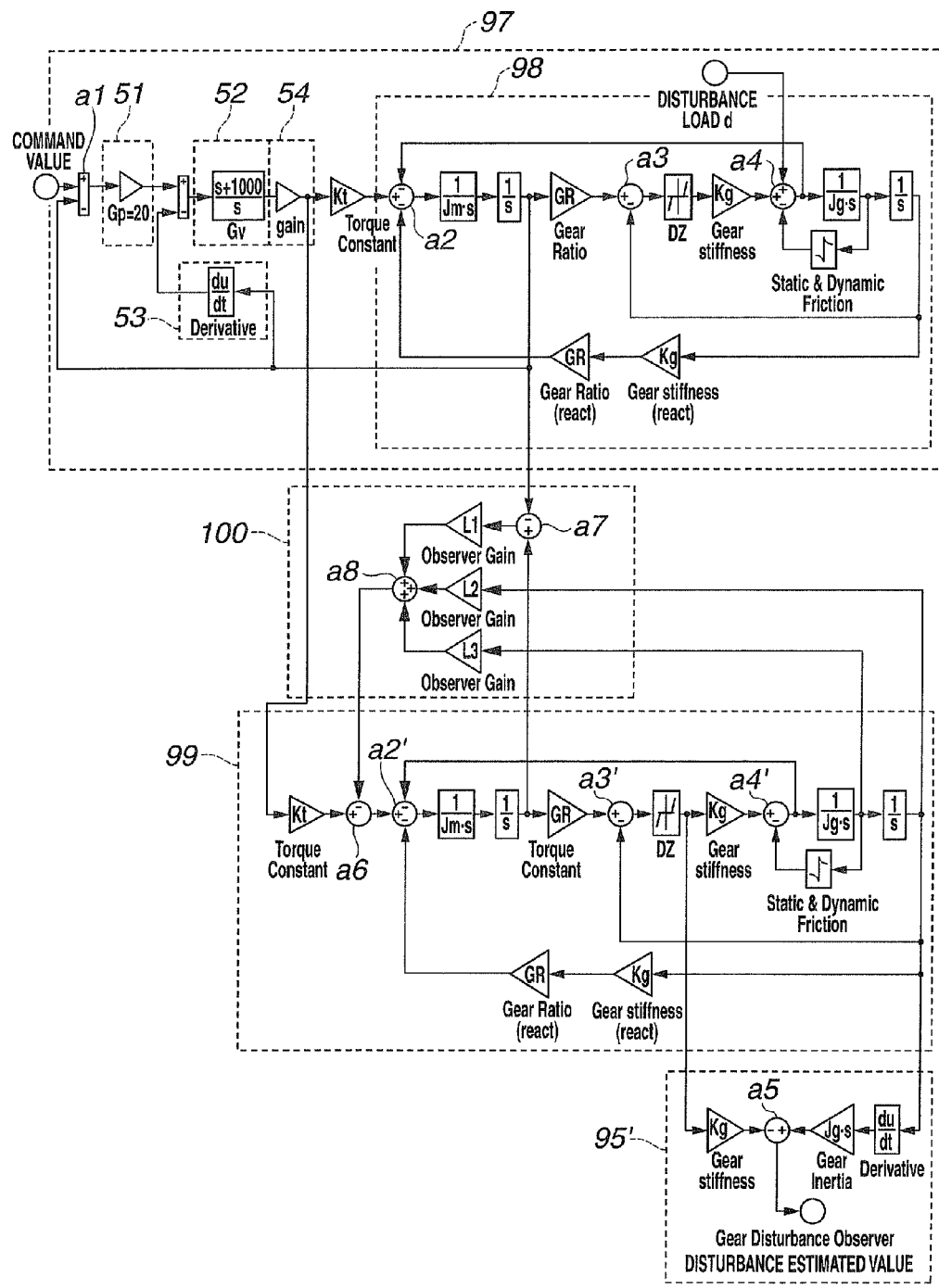
FIG. 23 is a block diagram showing a configuration of a motor driving system including a state estimation observer, etc. in embodiment 5 of the present invention.

Meanwhile, the configuration of the motor driving system in which the actual system including the gear section and an observer as a virtual model which simulates the actual system are built is shown in FIG. 23. In the configuration of FIG. 23, a part shown by numeral 97 in FIG. 23 coincides with the whole configuration of FIG. 20. In FIG. 23, a part shown by numeral 98 in 97 corresponds to the actual system.

And, in the present embodiment, a virtual model system 99 which simulates the actual system 98 and a state estimation observer 100 which connects the both systems and estimates the state amount are provided in the FPGA block 36.

Namely, in FIG. 23, all except the actual system 98 is configured in the FPGA 36 (in addition, more precisely a reaction part in the actual system 98 in FIG. 23 is in fact operated by the FPGA block 36).

As shown in FIG. 23, the virtual model system 99 performs simulation so as to be the same components as the actual system 98.

Note that, in FIG. 23, addition points a1-a4 in the actual system 98 are shown by addition points a1'-a4' in the virtual model system 99 for explanation.

Further, in the virtual model system 99, a torque estimation observer 95' corresponding to the gear disturbance observer 95 in the above-described embodiment 4 is additionally formed, and the torque estimation observer 95' makes a use of a sensor unnecessary and outputs a disturbance estimated value.

In addition, in the gear disturbance observer 95, the gear position information, for example, in the actual system 98 is utilized, whereas in the present embodiment, the gear position information in the virtual model system 99 is utilized. The configurations in operation processing by software are the same in the two embodiments.

Figure 24:
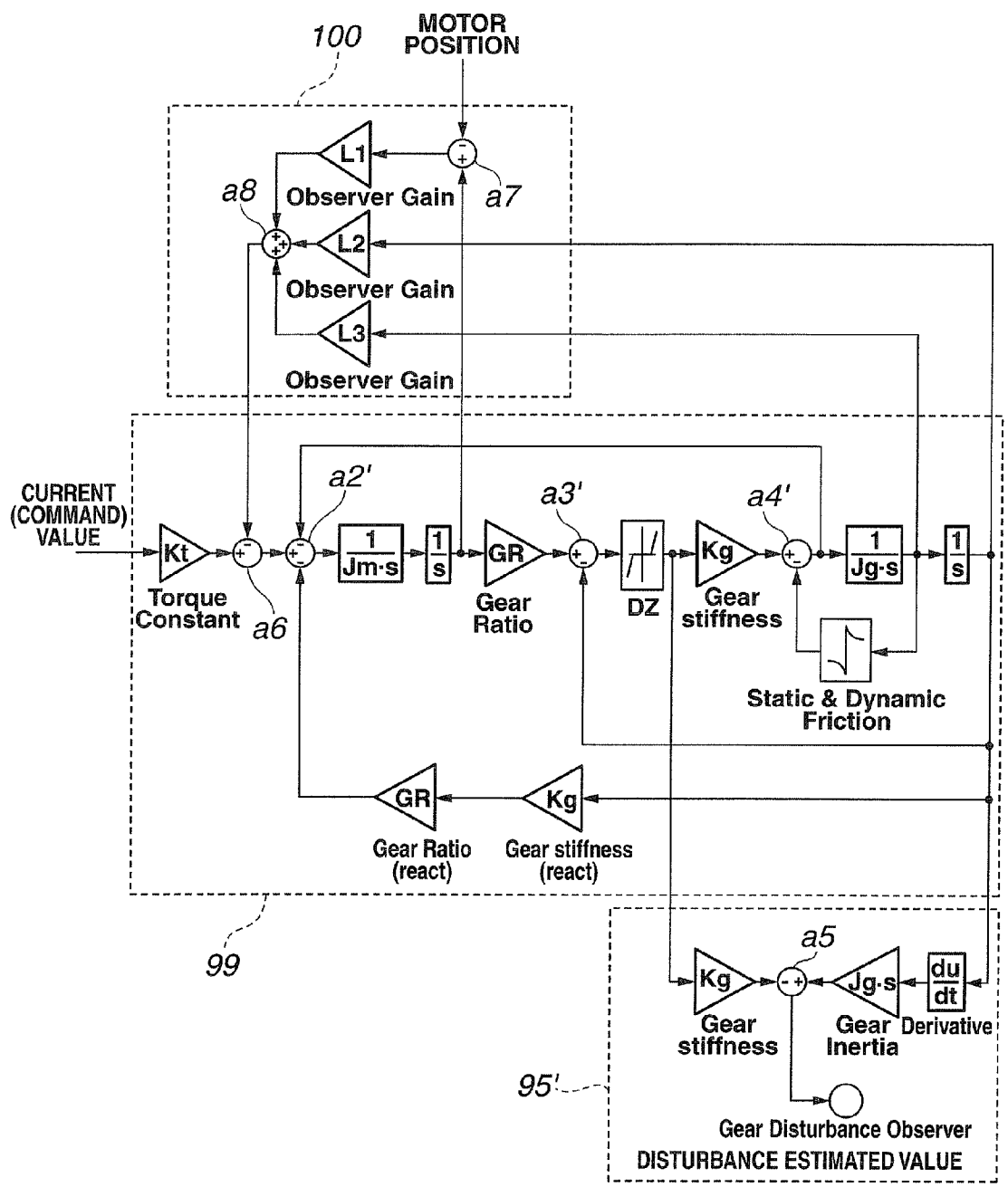
FIG. 24 is a block diagram showing a configuration of a virtual model system part including the state estimation observer and a torque estimation observer in FIG. 23.

FIG. 24 shows part of the virtual model system 99 including the torque estimation observer 95' and the state estimation observer 100 in FIG. 23.

In the virtual model system 99, a signal value passed through a current control block 54 (gain) in the actual system 98 is inputted into an addition point a2' and added. In this case, an addition point 26 subtracts an output signal value of a state estimation observer 100.

Further, the state estimation observer 100 has three gains L1, L2, L3 and a signal obtained by subtracting the motor position information in the actual system 98 from the motor position information in the virtual model system 99 through an addition point a7 is inputted into the gain L1. Further, the gear position information and the gear velocity information are inputted into the gains L2, L3, respectively.

And, output signals of the gains L1, L2, L3 are added together at an addition point a8 and outputted to an addition point a6 of the virtual model system 99.

As shown in FIG. 24, a state estimation observer 100 which simulates actions of the gears from a current (command) value (for driving the motor) and the motor position information is formed (in the FPGA block 36). Further, a toque estimation observer 95' for calculating a disturbance estimated value in the same manner as the case of the gear disturbance observer 95 is formed. And a disturbance estimated value is calculated by the toque estimation observer 95'.

As described above, in the state estimation observer 100, by feeding back the gear position information and the gear velocity information of the virtual model system 99 by the gains L2, L3, when the actual system 98 is simulated, it can be converged to the state of the actual system 98 in a short time by the virtual model system 99.

According to the present embodiment, since the disturbance load estimated value of the gear is calculated at the part closer to the gear side where the external force is actually acting rather than the case of torque detection at the motor side, the disturbance estimated value can be obtained with high precision.

Further, a response speed in a case of simulating the actual system 96 with high precision can be improved by configuration of forming a loop for feeding back a plurality of pieces of information in the virtual model system 99 in the state observer 100. Further, the calculated load value, etc. can be notified to a user such as operator by display, etc.

(Modified Example of Embodiment 5)

Figure 25:
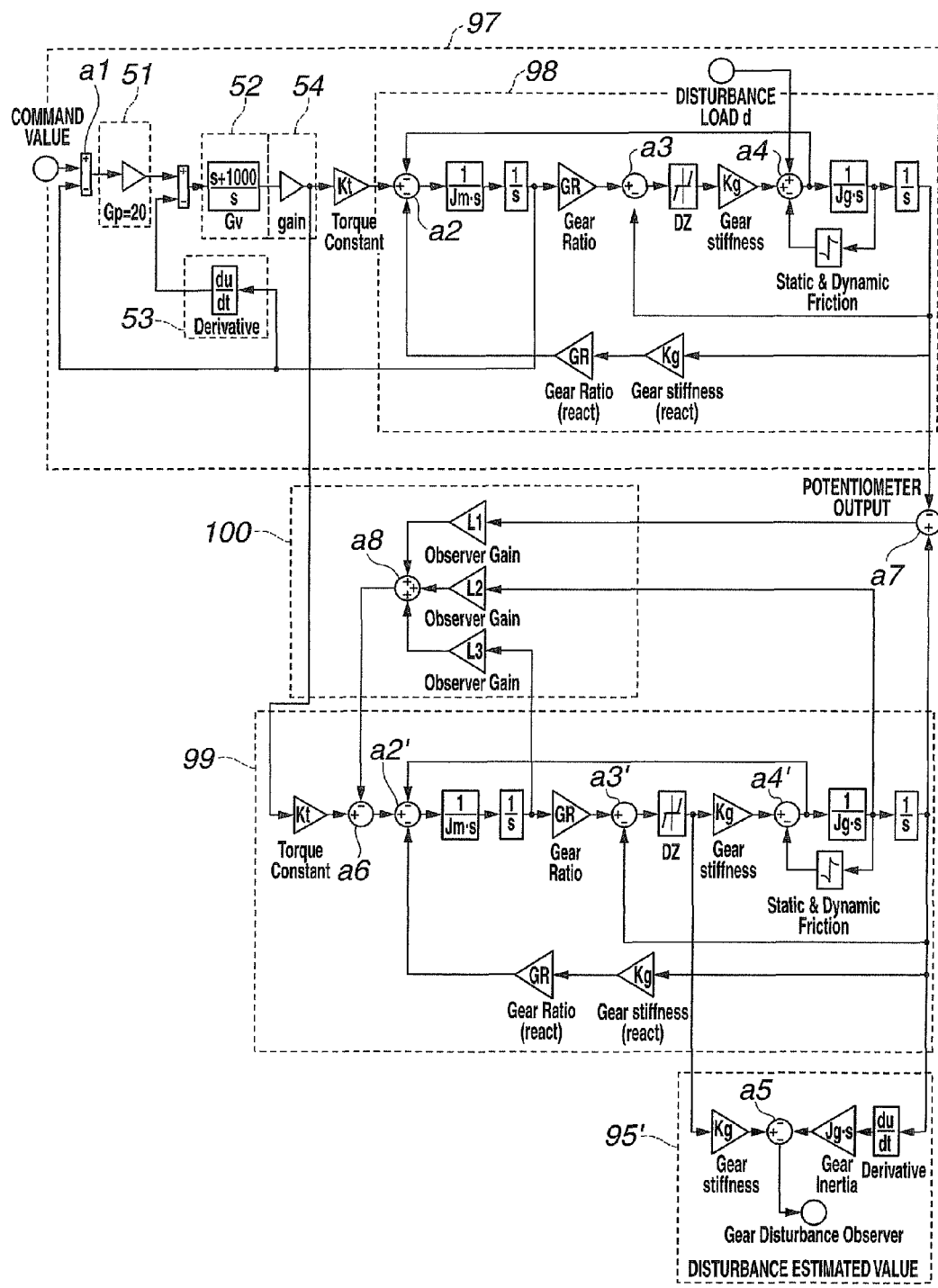
FIG. 25 is a block diagram showing a configuration of a motor driving system including a state estimation observer, etc. in a modified example of the embodiment 5.

FIG. 25 shows a block diagram of a motor unit driving system according to the modified example of embodiment 5.

In the state estimation observer 100 in the embodiment 5 as shown in FIG. 23, whereas motor position information (information of the encoder attached to the motor shaft in the actual system 98) is utilized, in the present embodiment it is configured that the gear position information (position information of the potentiometer 42 in the actual system 98) is utilized.

For this purpose, in the configuration of FIG. 25, a signal obtained by subtracting the gear position information of the actual system 98 from the gear position information of the virtual model system 99 at the addition point a7 is inputted into the gain L1.

Further, in the present modified example, the gear velocity information and the gear position information in the virtual model system 99 are inputted into the gains L2, L3, respectively.

The other configuration is the same as FIG. 23.

According to the present modified example, since the gear position information is utilized, the disturbance estimated value with high precision can be calculated. Further, in the case of configuration of FIG. 23, it can be widely applicable to a configuration without the potentiometer 42 and the disturbance estimated value with higher precision than that in the conventional example can be calculated.

Further, a different embodiment, etc. may be formed by partially combining the above described embodiments.

In addition, in the foregoing description, as a manipulator, an example of a case in which a bending portion as a tube body by connecting a plurality of bending pieces as movable bodies to be rotatable is bending controlled is explained, the present invention is not limited to this, but is widely applicable to a case of driving a tube body comprising a movable body by a motor.

What is claimed is:

1. A manipulator comprising:

an elongated tube body including a bendable bending portion;

a bending wire provided at the tube body for a bending operation of the bending portion;

a motor including a rotary shaft which rotates in accordance with a current command signal;

a reduction gear unit connected to the rotary shaft and configured by a plurality of gears meshing with each other for changing velocity with respect to a rotational velocity of the rotary shaft;

a connection portion which connects a proximal end of the bending wire and the reduction gear unit for operating the bending portion;

a motor angle detection unit which detects a rotational angle of the motor rotationally driven in accordance with the current command signal;

a reduction-gear-unit angle detection unit which detects a rotational angle of the reduction gear unit driven by the motor which is rotationally driven;

a torque information calculation section which calculates information of torque generated on the rotary shaft based on the rotational angle of the motor;

an estimated torque calculation section which calculates estimated torque information supposed to be generated on the rotary shaft by supplying the current command signal to a motor model of the motor;

a disturbance torque calculation section which calculates a difference between the torque information and the estimated torque information as information of disturbance torque generated on the rotary shaft;

a position data generation section which generates meshing positions of the plurality of gears as position data based on the rotational angle of the motor and the rotational angle of the reduction gear unit;

a storage unit which stores torque variation to be interposed with the disturbance torque to correspond to the position data and the disturbance torque information, as correction information in advance, the torque variation being periodically caused on the rotary shaft of the motor by the meshing of the plurality of gears constituting the reduction gear unit; and a tube body load calculation section which obtains the correction information from the storage unit and makes an operation for a load torque generated on the rotary shaft of the motor by a load exerted on the tube body, the load torque being obtained by correcting the disturbance torque information based on the correction information.

2. The manipulator according to claim 1, comprising a notification unit which notifies the load torque calculated by the tube body load calculation section.

3. The manipulator according to claim 1, comprising a judging section which judges whether the load torque belongs to a first state corresponding to the current command signal or to a second state in which an external force is acting to be deviated from the first state.

4. The manipulator according to claim 3, wherein the judging section judges whether or not reference information to be associated with the current command signal in advance and the load torque are deviated from each other by an allowable value or more by a comparator.

5. The manipulator according to claim 2, wherein the notification section superposes a signal for indicating the tube body load calculation result on a video signal of an image picked up by an image pickup element provided at a distal end of the tube body, and outputs the superposed signal to an endoscope image display unit.

6. The manipulator according to claim 1, further comprising a vibration signal component generator which superposes a vibration signal component having an amplitude to eliminate a static friction state of the plurality of gears constituting the reduction gear unit on the drive command signal to be applied to the motor when the current command signal is supplied to the motor.

7. The manipulator according to claim 1, comprising an average value calculating section which provides a vibration signal having an amplitude not to move the tube body while the current command signal is not supplied to the motor, and calculates an average value, in time, of an output value of the tube body load calculation section.

8. The manipulator according to claim 6, comprising an amplitude control section which variably controls the amplitude of the vibration signal to be lowered when the load torque calculated in the tube body load calculation section has a value in the vicinity of an approximately extreme ultimate value.

* * * * *